US011633117B2

(12) United States Patent
Weekly et al.

(10) Patent No.: US 11,633,117 B2
(45) Date of Patent: *Apr. 25, 2023

(54) MULTI-CHANNEL PHOTOPLETHYSMOGRAPHY SENSOR

(71) Applicant: Fitbit, Inc., San Francisco, CA (US)

(72) Inventors: Kevin Pu Weekly, San Leandro, CA (US); Subramaniam Venkatraman, Walnut Creek, CA (US); Andrew Larsen Axley, Mountain View, CA (US); Daniel J. Freschl, Berkeley, CA (US); Peter W. Richards, San Francisco, CA (US); Chris H. Sarantos, San Francisco, CA (US)

(73) Assignee: FITBIT, INC., San Francisco, CA (US)

( * ) Notice: Subject to any disclaimer, the term of this patent is extended or adjusted under 35 U.S.C. 154(b) by 236 days.

This patent is subject to a terminal disclaimer.

(21) Appl. No.: 16/592,599

(22) Filed: Oct. 3, 2019

(65) Prior Publication Data

US 2020/0138309 A1 May 7, 2020

Related U.S. Application Data

(63) Continuation of application No. 15/582,240, filed on Apr. 28, 2017, now Pat. No. 10,433,739.

(Continued)

(51) Int. Cl.
*A61B 5/024* (2006.01)
*A61B 5/00* (2006.01)

(52) U.S. Cl.
CPC ...... *A61B 5/02433* (2013.01); *A61B 5/02438* (2013.01); *A61B 5/681* (2013.01);
(Continued)

(58) Field of Classification Search
CPC .... A61B 5/02416–02444; A61B 5/681; A61B 5/7207–7214
See application file for complete search history.

(56) References Cited

U.S. PATENT DOCUMENTS

| 3,608,545 A | 9/1971 | Novack et al. |
| 4,258,719 A | 3/1981 | Lewyn |
| (Continued) | | |

FOREIGN PATENT DOCUMENTS

| CN | 1623175 A | 6/2005 |
| CN | 1729933 | 8/2006 |
| (Continued) | | |

OTHER PUBLICATIONS

U.S. Appl. No. 14/214,655, filed Mar. 14, 2014, Hong et al.
(Continued)

*Primary Examiner* — Thaddeus B Cox
(74) *Attorney, Agent, or Firm* — Dority & Manning, P.A.

(57) ABSTRACT

In one embodiment, a data processing method comprises obtaining one or more first photoplethysmography (PPG) signals based on one or more first light sources that are configured to emit light having a first light wavelength corresponding to a green light wavelength; obtaining one or more second PPG signals based on one or more second light sources that are configured to emit light having a second light wavelength corresponding to a red light wavelength, one or more of the first light sources and one or more of the second light sources being co-located; generating an estimated heart rate value based on one or more of the first PPG signals and the second PPG signals; and causing the estimated heart rate value to be displayed via a user interface on a client device.

20 Claims, 8 Drawing Sheets

Related U.S. Application Data

(60) Provisional application No. 62/329,861, filed on Apr. 29, 2016.

(52) U.S. Cl.
CPC .......... *A61B 5/6814* (2013.01); *A61B 5/6815* (2013.01); *A61B 5/7207* (2013.01); *A61B 5/7221* (2013.01)

(56) References Cited

U.S. PATENT DOCUMENTS

| | | |
|---|---|---|
| 4,367,752 A | 1/1983 | Jimenez et al. |
| 4,771,792 A | 9/1988 | Seale |
| 4,781,195 A | 11/1988 | Martin |
| 4,846,183 A | 7/1989 | Martin |
| 5,036,856 A | 8/1991 | Thornton |
| 5,101,831 A | 4/1992 | Koyama et al. |
| 5,301,154 A | 4/1994 | Suga |
| 5,318,597 A | 6/1994 | Hauck et al. |
| 5,490,523 A | 2/1996 | Isaacson et al. |
| 5,513,649 A | 5/1996 | Gevins et al. |
| 5,734,625 A | 3/1998 | Kondo |
| 5,738,104 A | 4/1998 | Lo et al. |
| 5,830,137 A | 11/1998 | Scharf |
| 5,954,644 A | 9/1999 | Dettling et al. |
| 6,076,015 A | 6/2000 | Hartley et al. |
| 6,099,478 A | 8/2000 | Aoshima et al. |
| 6,131,076 A | 10/2000 | Stephan et al. |
| 6,241,684 B1 | 6/2001 | Amano et al. |
| 6,289,230 B1 | 9/2001 | Chaiken et al. |
| 6,307,576 B1 | 10/2001 | Rosenfeld |
| 6,360,113 B1 | 3/2002 | Dettling |
| 6,402,690 B1 | 6/2002 | Rhee et al. |
| 6,418,394 B1 | 7/2002 | Puolakanaho et al. |
| 6,583,369 B2 | 6/2003 | Montagnino et al. |
| 6,585,622 B1 | 7/2003 | Shum et al. |
| 6,731,967 B1 | 5/2004 | Turcott |
| 6,882,955 B1 | 4/2005 | Ohlenbusch et al. |
| 6,959,259 B2 | 10/2005 | Vock et al. |
| 6,997,882 B1 | 2/2006 | Parker et al. |
| 7,020,508 B2 | 3/2006 | Stivoric et al. |
| 7,153,262 B2 | 12/2006 | Stivoric et al. |
| 7,171,331 B2 | 1/2007 | Vock et al. |
| 7,252,639 B2 | 8/2007 | Kimura et al. |
| 7,285,090 B2 | 10/2007 | Stivoric et al. |
| 7,334,472 B2 | 2/2008 | Seo et al. |
| 7,539,532 B2 | 5/2009 | Tran |
| 7,579,946 B2 | 8/2009 | Case, Jr. |
| 7,720,306 B2 | 5/2010 | Gardiner et al. |
| 7,909,768 B1 | 3/2011 | Turcott |
| 7,993,276 B2 | 8/2011 | Nazarian et al. |
| 8,040,758 B1 | 10/2011 | Dickinson |
| 8,073,707 B2 | 12/2011 | Teller et al. |
| 8,109,858 B2 | 2/2012 | Redmann |
| 8,140,143 B2 | 3/2012 | Picard et al. |
| 8,152,745 B2 | 4/2012 | Smith et al. |
| 8,157,731 B2 | 4/2012 | Teller et al. |
| 8,172,761 B1 | 5/2012 | Rulkov et al. |
| 8,199,126 B1 | 6/2012 | Taubman |
| 8,211,503 B2 | 7/2012 | Tsao et al. |
| 8,346,328 B2 | 1/2013 | Mannheimer et al. |
| 8,386,042 B2 | 2/2013 | Yudovsky et al. |
| 8,398,546 B2 | 3/2013 | Pacione et al. |
| 8,444,578 B2 | 5/2013 | Bourget et al. |
| 8,446,275 B2 | 5/2013 | Utter, II |
| 8,475,367 B1 | 7/2013 | Yuen et al. |
| 8,579,827 B1 | 11/2013 | Rulkov et al. |
| 8,641,612 B2 | 2/2014 | Teller et al. |
| 8,742,325 B1 | 6/2014 | Droz et al. |
| 8,792,981 B2 | 7/2014 | Yudovsky et al. |
| 8,868,377 B2 | 10/2014 | Yuen et al. |
| 8,886,269 B2 | 11/2014 | LeBoeuf et al. |
| 8,909,543 B2 | 12/2014 | Tropper et al. |
| 8,920,332 B2 | 12/2014 | Hong et al. |
| 8,923,941 B2 | 12/2014 | LeBoeuf et al. |
| 8,929,965 B2 | 1/2015 | LeBoeuf et al. |
| 8,936,552 B2 | 1/2015 | Kateraas et al. |
| 8,945,017 B2 | 2/2015 | Venkatraman et al. |
| 8,948,832 B2 | 2/2015 | Hong et al. |
| 8,954,135 B2 | 2/2015 | Yuen et al. |
| 8,956,303 B2 | 2/2015 | Hong et al. |
| 8,961,413 B2 | 2/2015 | Teller et al. |
| 8,989,830 B2 | 3/2015 | LeBoeuf et al. |
| 8,998,815 B2 | 4/2015 | Venkatraman et al. |
| 9,005,129 B2 | 4/2015 | Venkatraman et al. |
| 9,014,790 B2 | 4/2015 | Richards et al. |
| 9,031,812 B2 | 5/2015 | Roberts et al. |
| 9,042,971 B2 | 5/2015 | Brumback et al. |
| 9,044,149 B2 | 6/2015 | Richards et al. |
| 9,044,150 B2 | 6/2015 | Brumback et al. |
| 9,049,998 B2 | 6/2015 | Brumback et al. |
| 9,089,760 B2 | 7/2015 | Tropper et al. |
| 9,113,794 B2 | 8/2015 | Hong et al. |
| 9,113,795 B2 | 8/2015 | Hong et al. |
| 9,226,663 B2 | 1/2016 | Fei |
| 9,237,855 B2 | 1/2016 | Hong et al. |
| 9,282,902 B2 | 3/2016 | Richards et al. |
| 9,307,917 B2 | 4/2016 | Hong et al. |
| 9,314,166 B1 | 4/2016 | Brady et al. |
| 9,314,197 B2 | 4/2016 | Eisen et al. |
| 9,392,946 B1 | 7/2016 | Sarantos et al. |
| 9,402,552 B2 | 8/2016 | Richards et al. |
| 9,456,787 B2 | 10/2016 | Venkatraman et al. |
| 9,662,053 B2 | 5/2017 | Richards et al. |
| 9,775,548 B2 | 10/2017 | Sarantos et al. |
| 10,178,973 B2 | 1/2019 | Venkatraman et al. |
| 10,216,893 B2 | 2/2019 | Hong et al. |
| 10,216,894 B2 | 2/2019 | Hong et al. |
| 10,381,109 B2 | 8/2019 | Hong et al. |
| 10,433,739 B2 | 10/2019 | Weekly et al. |
| 10,512,407 B2 | 12/2019 | Richards et al. |
| 2001/0044588 A1 | 11/2001 | Mault |
| 2002/0077536 A1 | 6/2002 | Diab et al. |
| 2002/0091329 A1 | 7/2002 | Heikkila et al. |
| 2002/0139936 A1 | 10/2002 | Dumas |
| 2003/0107487 A1 | 6/2003 | Korman et al. |
| 2003/0128867 A1 | 7/2003 | Bennett |
| 2003/0163710 A1 | 8/2003 | Ortiz et al. |
| 2003/0229276 A1 | 12/2003 | Sarussi et al. |
| 2004/0171969 A1 | 9/2004 | Socci et al. |
| 2004/0190085 A1 | 9/2004 | Silverbrook et al. |
| 2004/0236227 A1 | 11/2004 | Gueissaz |
| 2005/0020927 A1 | 1/2005 | Blondeau et al. |
| 2005/0054940 A1 | 3/2005 | Almen |
| 2005/0209516 A1 | 9/2005 | Fraden |
| 2005/0245793 A1 | 11/2005 | Hilton et al. |
| 2005/0253047 A1 | 11/2005 | Maegawa et al. |
| 2006/0052727 A1 | 3/2006 | Palestrant |
| 2006/0195020 A1 | 8/2006 | Martin et al. |
| 2007/0213020 A1 | 9/2007 | Novac |
| 2007/0219059 A1 | 9/2007 | Schwartz et al. |
| 2007/0265533 A1 | 11/2007 | Tran |
| 2008/0039729 A1 | 2/2008 | Cho et al. |
| 2008/0097221 A1 | 4/2008 | Florian |
| 2008/0214360 A1 | 9/2008 | Stirling et al. |
| 2008/0214903 A1 | 9/2008 | Orbach |
| 2009/0012433 A1 | 1/2009 | Fernstrom et al. |
| 2009/0132197 A1 | 5/2009 | Rubin et al. |
| 2009/0143655 A1 | 6/2009 | Shani |
| 2009/0163783 A1 | 6/2009 | Mannheimer et al. |
| 2009/0292332 A1 | 11/2009 | Li et al. |
| 2009/0318779 A1 | 12/2009 | Tran |
| 2010/0026995 A1 | 2/2010 | Merritt et al. |
| 2010/0063365 A1 | 3/2010 | Pisani et al. |
| 2010/0079291 A1 | 4/2010 | Kroll et al. |
| 2010/0106044 A1 | 4/2010 | Linderman |
| 2010/0113948 A1 | 5/2010 | Yang et al. |
| 2010/0152600 A1 | 6/2010 | Droitcour et al. |
| 2010/0204550 A1 | 8/2010 | Heneghan et al. |
| 2010/0217102 A1 | 8/2010 | LeBoeuf et al. |
| 2010/0217103 A1 | 8/2010 | Abdul-Hafiz et al. |
| 2010/0240972 A1 | 9/2010 | Neal |
| 2010/0249633 A1 | 9/2010 | Droitcour et al. |

(56) References Cited

U.S. PATENT DOCUMENTS

| | | |
|---|---|---|
| 2010/0274100 A1 | 10/2010 | Behar et al. |
| 2010/0292568 A1 | 11/2010 | Droitcour et al. |
| 2010/0298650 A1 | 11/2010 | Moon et al. |
| 2010/0298651 A1 | 11/2010 | Moon et al. |
| 2010/0298653 A1 | 11/2010 | McCombie et al. |
| 2010/0298661 A1 | 11/2010 | McCombie et al. |
| 2010/0331145 A1 | 12/2010 | Lakovic et al. |
| 2010/0331657 A1 | 12/2010 | Mensinger et al. |
| 2011/0009727 A1 | 1/2011 | Mensinger et al. |
| 2011/0032105 A1 | 2/2011 | Hoffman et al. |
| 2011/0066010 A1 | 3/2011 | Moon et al. |
| 2011/0112442 A1 | 5/2011 | Meger et al. |
| 2011/0118621 A1 | 5/2011 | Chu |
| 2011/0237911 A1 | 9/2011 | Lamego et al. |
| 2011/0237912 A1 | 9/2011 | Couronne et al. |
| 2011/0263950 A1 | 10/2011 | Larson et al. |
| 2011/0276304 A1 | 11/2011 | Yin et al. |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0123232 A1 | 5/2012 | Najarian et al. |
| 2012/0140233 A1 | 6/2012 | Rockwell et al. |
| 2012/0143067 A1 | 6/2012 | Watson et al. |
| 2012/0150052 A1 | 6/2012 | Buchheim et al. |
| 2012/0150074 A1 | 6/2012 | Yanev et al. |
| 2012/0172733 A1 | 7/2012 | Park |
| 2012/0226471 A1 | 9/2012 | Yuen et al. |
| 2012/0226472 A1 | 9/2012 | Yuen et al. |
| 2012/0232432 A1 | 9/2012 | Kahn et al. |
| 2012/0245439 A1 | 9/2012 | Andre et al. |
| 2012/0253486 A1 | 10/2012 | Niemimaki |
| 2012/0255875 A1 | 10/2012 | Vicente et al. |
| 2012/0271180 A1 | 10/2012 | Ren et al. |
| 2012/0274508 A1 | 11/2012 | Brown et al. |
| 2012/0316471 A1 | 12/2012 | Rahman et al. |
| 2013/0009779 A1 | 1/2013 | Wittling et al. |
| 2013/0053661 A1 | 2/2013 | Alberth et al. |
| 2013/0073254 A1 | 3/2013 | Yuen et al. |
| 2013/0073255 A1 | 3/2013 | Yuen et al. |
| 2013/0077823 A1 | 3/2013 | Mestha et al. |
| 2013/0077826 A1 | 3/2013 | Cowperthwaite et al. |
| 2013/0079607 A1 | 3/2013 | Gareau et al. |
| 2013/0080113 A1 | 3/2013 | Yuen et al. |
| 2013/0106684 A1 | 5/2013 | Weast et al. |
| 2013/0151196 A1 | 6/2013 | Yuen et al. |
| 2013/0158369 A1 | 6/2013 | Yuen et al. |
| 2013/0173171 A1 | 7/2013 | Drysdale et al. |
| 2013/0191034 A1 | 7/2013 | Weast et al. |
| 2013/0211265 A1 | 8/2013 | Bedingham et al. |
| 2013/0218053 A1 | 8/2013 | Kaiser et al. |
| 2013/0245436 A1 | 9/2013 | Tupin, Jr. et al. |
| 2014/0039284 A1 | 2/2014 | Niwayama et al. |
| 2014/0073486 A1 | 3/2014 | Ahmed et al. |
| 2014/0074431 A1 | 3/2014 | Modi |
| 2014/0099614 A1 | 4/2014 | Hu et al. |
| 2014/0107493 A1 | 4/2014 | Yuen et al. |
| 2014/0135612 A1 | 5/2014 | Yuen et al. |
| 2014/0135631 A1 | 5/2014 | Brumback et al. |
| 2014/0142403 A1 | 5/2014 | Brumback et al. |
| 2014/0180158 A1 | 6/2014 | Cheng et al. |
| 2014/0228649 A1 | 8/2014 | Rayner |
| 2014/0241626 A1 | 8/2014 | Sull et al. |
| 2014/0275821 A1 | 9/2014 | Beckman |
| 2014/0275852 A1 | 9/2014 | Hong et al. |
| 2014/0275854 A1 | 9/2014 | Venkatraman et al. |
| 2014/0276119 A1 | 9/2014 | Venkatraman et al. |
| 2014/0278139 A1 | 9/2014 | Hong et al. |
| 2014/0288390 A1 | 9/2014 | Hong et al. |
| 2014/0288391 A1 | 9/2014 | Hong et al. |
| 2014/0288392 A1 | 9/2014 | Hong et al. |
| 2014/0288435 A1 | 9/2014 | Richards et al. |
| 2014/0288436 A1 | 9/2014 | Venkatraman et al. |
| 2014/0288438 A1 | 9/2014 | Venkatraman et al. |
| 2014/0303523 A1 | 10/2014 | Hong et al. |
| 2014/0378786 A1 | 12/2014 | Hong et al. |
| 2014/0378787 A1 | 12/2014 | Brumback et al. |
| 2014/0378844 A1 | 12/2014 | Fei |
| 2014/0378872 A1 | 12/2014 | Hong et al. |
| 2015/0025393 A1 | 1/2015 | Hong et al. |
| 2015/0025394 A1 | 1/2015 | Hong et al. |
| 2015/0173631 A1 | 6/2015 | Richards et al. |
| 2015/0196256 A1 | 7/2015 | Venkatraman et al. |
| 2015/0201853 A1 | 7/2015 | Hong et al. |
| 2015/0201854 A1 | 7/2015 | Hong et al. |
| 2015/0223708 A1 | 8/2015 | Richards et al. |
| 2015/0230743 A1 | 8/2015 | Silveira et al. |
| 2015/0230761 A1 | 8/2015 | Brumback et al. |
| 2015/0282713 A1 | 10/2015 | Fei |
| 2015/0313549 A1* | 11/2015 | Lee ........................ A61B 5/721 |
| | | 600/479 |
| 2015/0351688 A1 | 12/2015 | Just et al. |
| 2015/0366469 A1 | 12/2015 | Harris et al. |
| 2015/0366504 A1 | 12/2015 | Connor et al. |
| 2016/0007929 A1* | 1/2016 | Chuang ................ A61B 5/7214 |
| | | 600/324 |
| 2016/0029968 A1 | 2/2016 | Lerner et al. |
| 2016/0034634 A9 | 2/2016 | Hong et al. |
| 2016/0058309 A1 | 3/2016 | Han |
| 2016/0058312 A1 | 3/2016 | Han et al. |
| 2016/0113585 A1 | 4/2016 | Uedaira et al. |
| 2016/0183818 A1 | 6/2016 | Richards et al. |
| 2016/0287108 A1 | 6/2016 | Richards et al. |
| 2016/0302706 A1 | 10/2016 | Richards et al. |
| 2016/0345881 A1 | 12/2016 | Sarantos et al. |
| 2017/0020659 A1 | 1/2017 | Hyde et al. |
| 2017/0027523 A1 | 2/2017 | Venkatraman et al. |
| 2017/0065178 A1 | 3/2017 | Suzuki et al. |
| 2017/0118551 A1 | 4/2017 | Wagner et al. |
| 2017/0120107 A1 | 5/2017 | Wisbey |
| 2017/0150919 A1 | 6/2017 | Chuang et al. |
| 2017/0164848 A1 | 6/2017 | Nadeau et al. |
| 2017/0311825 A1 | 11/2017 | Weekly et al. |
| 2018/0020960 A1 | 1/2018 | Sarussi et al. |
| 2018/0020979 A1 | 1/2018 | Wagner et al. |
| 2018/0108802 A1 | 4/2018 | Chen |
| 2018/0310846 A1 | 11/2018 | Lin |
| 2019/0082985 A1 | 3/2019 | Hong et al. |
| 2019/0385708 A1 | 12/2019 | Hong et al. |

FOREIGN PATENT DOCUMENTS

| | | |
|---|---|---|
| CN | 100362963 C | 1/2008 |
| CN | 101615098 A | 12/2009 |
| CN | 101730503 | 6/2010 |
| CN | 101742981 A | 6/2010 |
| CN | 102008811 A | 4/2011 |
| CN | 202069586 U | 12/2011 |
| CN | 102389313 A | 3/2012 |
| CN | 102551686 A | 7/2012 |
| CN | 102750015 A | 10/2012 |
| CN | 102781310 A | 11/2012 |
| CN | 103093420 A | 5/2013 |
| CN | 105 266 786 A | 1/2016 |
| EP | 1297784 A1 | 4/2003 |
| EP | 1586353 A1 | 10/2005 |
| EP | 1 721 237 | 8/2012 |
| EP | 1721237 | 8/2012 |
| WO | WO 2014/091424 A2 | 6/2014 |
| WO | WO 2014/091424 A3 | 6/2014 |
| WO | WO 2017190051 | 11/2017 |

OTHER PUBLICATIONS

U.S. Appl. No. 15/494,257, filed Apr. 21, 2017, Richards et al.
U.S. Office Action, dated Aug. 4, 2014, issued in U.S. Appl. No. 13/924,784.
U.S. Notice of Allowance, dated Nov. 19, 2014, issued in U.S. Appl. No. 13/924,784.
U.S. Office Action, dated Oct. 22, 2014, issued in U.S. Appl. No. 14/290,884.

(56) References Cited

OTHER PUBLICATIONS

U.S. Notice of Allowance, dated Feb. 6, 2015, issued in U.S. Appl. No. 14/290,884.
U.S. Office Action, dated Jun. 22, 2015, issued in U.S. Appl. No. 14/693,710.
U.S. Notice of Allowance, dated Jul. 27, 2015, issued in U.S. Appl. No. 14/639,710.
U.S. Notice of Allowance, dated Apr. 15, 2016, issued in U.S. Appl. No. 14/954,753.
U.S. Office Action, dated Oct. 26, 2016, issued in U.S. Appl. No. 15/195,911.
U.S. Notice of Allowance, dated Jan. 23, 2017, issued in U.S. Appl. No. 15/195,911.
U.S. Notice of Allowance, dated Sep. 23, 2014, issued in U.S. Appl. No. 14/292,669.
U.S. Notice of Allowance (Corrected Notice of Allowability), dated Oct. 14, 2014, issued in U.S. Appl. No. 14/292,669.
U.S. Notice of Allowance (Corrected Notice of Allowability), dated Dec. 31, 2014, issued in U.S. Appl. No. 14/292,669.
U.S. Notice of Allowance, dated Oct. 14, 2014, issued in U.S. Appl. No. 14/295,144.
U.S. Notice of Allowance, dated Dec. 3, 2014, issued in U.S. Appl. No. 14/295,144.
U.S. Notice of Allowance, dated Sep. 26, 2014, issued in U.S. Appl. No. 14/295,158.
U.S. Notice of Allowance (Corrected Notice of Allowability), dated Dec. 31, 2014, issued in U.S. Appl. No. 14/295,158.
U.S. Office Action, dated Jan. 23, 2015, issued in U.S. Appl. No. 14/507,184.
U.S. Final Office Action, dated May 11, 2015, issued in U.S. Appl. No. 14/507,184.
U.S. Notice of Allowance, dated Aug. 11, 2015, issued in U.S. Appl. No. 14/507,184.
U.S. Notice of Allowance (Corrected Notice of Allowability), dated Dec. 18, 2015, issued in U.S. Appl. No. 14/507,184.
U.S. Office Action, dated Jan. 26, 2015, issued in U.S. Appl. No. 14/295,161.
U.S. Notice of Allowance, dated Apr. 14, 2015, issued in U.S. Appl. No. 14/295,161.
U.S. Notice of Allowance, dated Jul. 28, 2015, issued in U.S. Appl. No. 14/295,161.
U.S. Office Action, dated May 11, 2015, issued in U.S. Appl. No. 14/673,630.
U.S. Notice of Allowance, dated Nov. 25, 2015, issued in U.S. Appl. No. 14/673,630.
U.S. Notice of Allowance (Corrected Notice of Allowability), dated Mar. 21, 2016, issued in U.S. Appl. No. 14/673,630.
U.S. Office Action, dated Jan. 27, 2015, issued in U.S. Appl. No. 14/507,173.
U.S. Notice of Allowance, dated Apr. 17, 2015, issued in U.S. Appl. No. 14/507,173.
U.S. Notice of Allowance (Corrected Notice of Allowability), dated Jul. 16, 2015, issued in U.S. Appl. No. 14/507,173.
U.S. Office Action, dated Jun. 8, 2015, issued in U.S. Appl. No. 14/673,634.
U.S. Final Office Action, dated Nov. 4, 2015, issued in U.S. Appl. No. 14/673,634.
U.S. Office Action, dated Jul. 13, 2016, issued in U.S. Appl. No. 14/673,634.
U.S. Office Action, dated Feb. 9, 2017, issued in U.S. Appl. No. 14/673,634.
U.S. Final Office Action, dated Aug. 9, 2017, issued in U.S. Appl. No. 14/673,634.
U.S. Office Action, dated Mar. 27, 2018, issued in U.S. Appl. No. 14/673,634.
U.S. Office Action, dated Aug. 5, 2014, issued in U.S. Appl. No. 14/292,673.
U.S. Notice of Allowance, dated Dec. 8, 2014, issued in U.S. Appl. No. 14/292,673.
U.S. Notice of Allowance (Corrected Notice of Allowability), dated Mar. 5, 2015, issued in U.S. Appl. No. 14/292,673.
U.S. Office Action, dated Sep. 18, 2014, issued in U.S. Appl. No. 14/295,059.
U.S. Notice of Allowance, dated Jan. 28, 2015, issued in U.S. Appl. No. 14/295,059.
U.S. Notice of Allowance (Corrected Notice of Allowability), dated Mar. 11, 2015, issued in U.S. Appl. No. 14/295,059.
U.S. Office Action, dated Dec. 24, 2014, issued in U.S. Appl. No. 14/295,076.
U.S. Final Office Action, dated Apr. 15, 2015, issued in U.S. Appl. No. 14/295,076.
U.S. Office Action, dated Oct. 22, 2015, issued in U.S. Appl. No. 14/295,076.
U.S. Notice of Allowance, dated May 24, 2016, issued in U.S. Appl. No. 14/295,076.
U.S. Office Action, dated Jan. 12, 2018, issued in U.S. Appl. No. 15/246,387.
U.S. Notice of Allowance, dated Aug. 29, 2018, issued in U.S. Appl. No. 15/246,387.
U.S. Office Action, dated Jul. 31, 2014, issued in U.S. Appl. No. 14/295,122.
U.S. Notice of Allowance, dated Nov. 24, 2014, issued in U.S. Appl. No. 14/295,122.
U.S. Notice of Allowance (Corrected Notice of Allowability), dated Jan. 5, 2015, issued in U.S. Appl. No. 14/295,122.
U.S. Office Action dated Dec. 22, 2016, issued in U.S. Appl. No. 14/599,039.
U.S. Final Office Action dated Aug. 3, 2017, issued in U.S. Appl. No. 14/599,039.
U.S. Office Action, dated Mar. 14, 2014, issued in U.S. Appl. No. 14/154,009.
U.S. Office Action, dated Sep. 29, 2014, issued in U.S. Appl. No. 14/154,009.
U.S. Notice of Allowance, dated Jan. 21, 2015, issued in U.S. Appl. No. 14/154,009.
U.S. Office Action, dated Nov. 25, 2014, issued in U.S. Appl. No. 14/154,019.
U.S. Notice of Allowance, dated Mar. 20, 2015, issued in U.S. Appl. No. 14/154,019.
U.S. Notice of Allowance (Corrected Notice of Allowability), dated May 14, 2015, issued in U.S. Appl. No. 14/154,019.
U.S. Office Action, dated Jul. 24, 2018, issued in U.S. Appl. No. 14/696,256.
U.S. Final Office Action, dated Feb. 26, 2019, issued in U.S. Appl. No. 14/696,256.
U.S. Office Action, dated Feb. 19, 2020, issued in U.S. Appl. No. 14/696,256.
U.S. Office Action, dated Dec. 10, 2014, issued in U.S. Appl. No. 14/484,104.
U.S. Notice of Allowance, dated Mar. 19, 2015, issued in U.S. Appl. No. 14/484,104.
U.S. Notice of Allowance (Corrected Notice of Allowability), dated May 6, 2015, issued in U.S. Appl. No. 14/484,104.
U.S. Office Action, dated Dec. 4, 2014, issued in U.S. Appl. No. 14/216,743.
U.S. Final Office Action, dated Apr. 8, 2015, issued in U.S. Appl. No. 14/216,743.
U.S. Office Action, dated Oct. 2, 2015, issued in U.S. Appl. No. 14/216,743.
U.S. Final Office Action, dated Feb. 8, 2016, issued in U.S. Appl. No. 14/216,743.
U.S. Office Action, dated May 16, 2016, issued in U.S. Appl. No. 14/216,743.
U.S. Office Action, dated Jan. 13, 2017, issued in U.S. Appl. No. 14/216,743.
U.S. Examiner's Answer to Appeal Brief before the Patent Trial and Appeal Board [in response to the appeal brief filed Sep. 12, 2017 appealing from the Office action mailed Jan. 3, 2017], dated Nov. 30, 2017, issued in U.S. Appl. No. 14/216,743.
U.S. Patent Trial and Appeal Board's Decision on Appeal, dated Oct. 9, 2018, issued in U.S. Appl. No. 14/216,743.

(56) References Cited

OTHER PUBLICATIONS

U.S. Notice of Allowance, dated Dec. 17, 2018, issued in U.S. Appl. No. 14/216,743.
U.S. Office Action, dated Mar. 12, 2015, issued in U.S. Appl. No. 14/481,020.
U.S. Final Office Action, dated Jul. 7, 2015, issued in U.S. Appl. No. 14/481,020.
U.S. Office Action, dated Oct. 27, 2015, issued in U.S. Appl. No. 14/481,020.
U.S. Final Office Action, dated May 13, 2016, issued in U.S. Appl. No. 14/481,020.
U.S. Examiner's Answer to Appeal Brief before the Patent Trial and Appeal Board [in response to the appeal brief filed Dec. 9, 2016 appealing from the Office action dated May 13, 2016], dated Jan. 23, 2017, issued in U.S. Appl. No. 14/481,020.
U.S. Patent Trial and Appeal Board's Decision on Appeal, dated Sep. 14, 2018, issued in U.S. Appl. No. 14/481,020.
U.S. Notice of Allowance, dated Nov. 29, 2018, issued in U.S. Appl. No. 14/481,020.
U.S. Office Action, dated Aug. 22, 2014, issued in U.S. Appl. No. 14/250,256.
U.S. Final Office Action, dated Nov. 21, 2014, issued in U.S. Appl. No. 14/250,256.
U.S. Office Action, dated Jul. 8, 2015, issued in U.S. Appl. No. 14/250,256
U.S. Final Office Action, dated Oct. 23, 2015, issued in U.S. Appl. No. 14/250,256.
U.S. Office Action, dated Mar. 17, 2016, issued in U.S. Appl. No. 14/250,256.
U.S. Final Office Action, dated Jun. 29, 2016, issued in U.S. Appl. No. 14/250,256.
U.S. Office Action, dated Jan. 9, 2017, issued in U.S. Appl. No. 14/250,256.
U.S. Examiner's Answer to the Appeal Brief before the Patent Trial and Appeal Board [in response to the appeal brief filed Jul. 11, 2017 appealing from the Office action dated Jan. 7, 2017], dated Aug. 24, 2017, issued in U.S. Appl. No. 14/250,256.
U.S. Patent Trial and Appeal Board's Decision on Appeal, dated Oct. 9, 2018, issued in U.S. Appl. No. 14/250,256.
U.S. Notice of Allowance, dated Mar. 29, 2019, issued in U.S. Appl. No. 14/250,256.
U.S. Office Action, dated Oct. 7, 2014, issued in U.S. Appl. No. 14/481,762.
U.S. Final Office Action, dated Dec. 19, 2014, issued in U.S. Appl. No. 14/481,762.
U.S. Office Action, dated Jul. 7, 2015, issued in U.S. Appl. No. 14/481,762.
U.S. Final Office Action, dated Nov. 5, 2015, issued in U.S. Appl. No. 14/481,762.
U.S. Office Action, dated May 11, 2016, issued in U.S. Appl. No. 14/481,762.
U.S. Final Office Action, dated Oct. 19, 2016, issued in U.S. Appl. No. 14/481,762.
U.S. Office Action, dated Apr. 12, 2017, issued in U.S. Appl. No. 14/481,762.
U.S. Office Action, dated Nov. 19, 2015, issued in U.S. Appl. No. 14/724,750.
U.S. Notice of Allowance, dated Mar. 8, 2016, issued in U.S. Appl. No. 14/724,750.
U.S. Office Action dated Sep. 8, 2016, issued in U.S. Appl. No. 15/192,447.
U.S. Final Office Action dated Feb. 7, 2017, issued in U.S. Appl. No. 15/192,447.
U.S. Notice of Allowance dated May 24, 2017, issued in U.S. Appl. No. 15/192,447.
U.S. Office Action dated Mar. 15, 2017, issued in U.S. Appl. No. 15/370,303.
U.S. Final Office Action dated Aug. 1, 2017, issued in U.S. Appl. No. 15/370,303.
U.S. Office Action dated Jan. 11, 2018, issued in U.S. Appl. No. 15/370,303.
U.S. Final Office Action dated Jul. 25, 2018, issued in U.S. Appl. No. 15/370,303.
U.S. Office Action dated May 24, 2019, issued in U.S. Appl. No. 15/370,303.
U.S. Office Action, dated Oct. 7, 2014, issued in U.S. Appl. No. 14/292,844.
U.S. Notice of Allowance, dated Feb. 9, 2015, issued in U.S. Appl. No. 14/292,844.
U.S. Office Action, dated Jul. 6, 2015, issued in U.S. Appl. No. 14/640,281.
U.S. Final Office Action, dated Nov. 12, 2015, issued in U.S. Appl. No. 14/640,281.
U.S. Office Action, dated Oct. 6, 2016, issued in U.S. Appl. No. 14/640,281.
U.S. Final Office Action, dated May 4, 2017, issued in U.S. Appl. No. 14/640,281.
U.S. Office Action, dated Jun. 29, 2018, issued in U.S. Appl. No. 14/640,281.
U.S. Final Office Action, dated Feb. 21, 2019, issued in U.S. Appl. No. 14/640,281.
U.S. Notice of Allowance, dated Aug. 2, 2019, issued in U.S. Appl. No. 14/640,281.
U.S. Office Action, dated Mar. 11, 2019, issued in U.S. Appl. No. 15/582,240.
U.S. Notice of Allowance, dated Jun. 14, 2019, issued in U.S. Appl. No. 15/582,240.
Chinese First Office Action dated Sep. 27, 2016 issued in Application No. CN 201410018701.8.
Chinese Second Office Action dated Jun. 13, 2017 issued in Application No. CN 201410018701.8.
Chinese First Office Action dated Aug. 7, 2015 issued in Application No. CN 201410243180.6.
Chinese First Office Action dated Sep. 2, 2016 issued in Application No. CN 201510745382.5.
Chinese Second Office Action dated Mar. 22, 2017 issued in Application No. CN 201510745382.5.
Chinese First Office Action dated Mar. 22, 2018 issued in Application No. CN 201610284612.7.
Chinese Second Office Action dated Nov. 6, 2018 issued in Application No. CN 201610284612.7.
Chinese First Office Action dated Aug. 3, 2016 issued in Application No. CN 201410243169.X.
Chinese Second Office Action dated Mar. 27, 2017 issued in Application No. CN 201410243169.X.
Chinese Third Office Action dated Sep. 28, 2017 issued in Application No. CN 201410243169.X.
Chinese First Office Action dated Sep. 26, 2016 issued in Application No. CN 201410243178.9.
Chinese Second Office Action dated Jun. 15, 2017 issued in Application No. CN 201410243178.9.
Chinese First Office Action dated Mar. 3, 2017 issued in Application No. CN 201610622453.7.
Chinese Second Office Action dated Sep. 19, 2017 issued in Application No. CN 201610622453.7.
Chinese Third Office Action dated Jan. 24, 2018 issued in Application No. CN 201610622453.7.
Chinese Fourth Office Action dated Jun. 1, 2018 issued in Application No. CN 201610622453.7.
Chinese First Office Action dated Jul. 13, 2017 issued in Application No. CN 201610621114.7.
Chinese Second Office Action dated Apr. 9, 2018 issued in Application No. CN 201610621114.7.
Chinese Third Office Action dated Sep. 14, 2018 issued in Application No. CN 201610621114.7.
Chinese First Office Action dated Jan. 14, 2019 issued in Application No. CN 201510117698.X.
Chinese First Office Action dated Jan. 22, 2020, issued in Application No. CN 201780033558.1.
European Extended Search Report dated Oct. 25, 2016 issued in Application No. EP 16 16 8661.3.

(56) References Cited

OTHER PUBLICATIONS

European Office Action dated Mar. 19, 2019 issued in Application No. EP 16 16 8661.3.
European Extended Search Report dated Sep. 9, 2019, issued in Application No. EP 17790575.9.
International Search Report and Written Opinion—PCT/US2017/030190—ISA/US—dated Jul. 7, 2017 (Jul. 7, 2017).
Litigation Document—"Complaint for Patent Infringement," filed Sep. 3, 2015, in U.S. District Court of Delaware (Court Docket No. 1: 15-cv-00775-RGA).
Litigation Document—"Report on the Filing or Determination of an Action Regarding a Patent or Trademark," filed Sep. 3, 2015, in U.S. District Court of Delaware (Court Docket No. 1: 15-cv-00775-RGA).
Litigation Document—"Complaint for Patent Infringement," filed Oct. 29, 2015, in U.S. District Court of Delaware (Court Docket No. 1:15-cv-00990-RGA) [Re: U.S. Pat. Nos. 8,868,377, 8,920,332, and 9,089,760].
Litigation Document—"Report on the Filing or Determination of an Action Regarding a Patent or Trademark," filed Oct. 29, 2015, in U.S. District Court of Delaware (Court Docket No. 1:15-cv-00990-RGA) [Re: U.S. Pat. Nos. 8,868,377, 8,920,332, and 9,089,760].
Litigation Document—"Order No. 24: Initial Determination Granting Respondents' Motion for Summary Determination of Invalidity under 35 U.S.C. § 101 with respect to all Three Asserted Patents and Terminating the Investigation in its Entirety," filed Jul. 19, 2016, in United States International Trade Commission, Washington, D.C. (Investigation No. 337-TA-973) [in the Matter of Certain Wearable Activity Tracking Devices, Systems, and Components Thereof].
Litigation Document—"Respondents' Opposition to Complainant's Petition for Review of the Initial Determination Granting Summary Determination that the Asserted Patents are Directed to Ineligible Subject Matter under 35 U.S.C. § 101," filed Aug. 8, 2016, in United States International Trade Commission, Washington, D.C. (Investigation No. 337-TA-973) (4446833v1/014972) [in the Matter of Certain Wearable Activity Tracking Devices, Systems, and Components Thereof].
Litigation Document—"Declaration of Majid Sarrafzadeh in Support of Complainant's Brief in Opposition to Respondents' Motion for Summary Determination that the Asserted Patents are Directed to Ineligible Subject Matter under 35 U.S.C. § 101," filed Jun. 2, 2016, in United States International Trade Commission, Washington, D.C. (Investigation No. 37-TA-973) [in the Matter of Certain Wearable Activity Tracking Devices, Systems, and Components Thereof] [Exhibit 7].
Litigation Document—"Kiaei Declaration in Support of Complainant's Supplemental Brief Regarding Construction of Operating the Heart Rate Monitor in a Worn Detection Mode under 35 U.S.C. § 112(f)," filed Apr. 29, 2016, in United States International Trade Commission, Washington, D.C. (Investigation No. 37-TA-973) [In the Matter of Certain Wearable Activity Tracking Devices, Systems, and Components Thereof] [Exhibit 8].
Litigation Document—"Memorandum in Support of Respondents' Motion for Summary Determination that the Asserted Patents are Directed to Ineligible Subject Matter under 35 U.S.C. § 101," filed May 23, 2016, in United States International Trade Commission, Washington, D.C. (Investigation No. 337-TA-973) (44325007v1/014972) [in the Matter of Certain Wearable Activity Tracking Devices, Systems, and Components Thereof].
Litigation Document—"Grimes Declaration in Support of Complainant's Brief in Opposition to Respondents' Motion for Summary Determination that the Asserted Patents are Directed to Ineligible Subject Matter under 35 U.S.C. § 101," filed Jun. 2, 2016, in United States International Trade Commission, Washington, D.C. (Investigation No. 37-TA-973) [in the Matter of Certain Wearable Activity Tracking Devices, Systems, and Components Thereof] [Exhibit 28].
Litigation Document—"Complainant's Brief in Opposition to Respondents' Motion for Summary Determination that the Asserted Patents are Directed to Ineligible Subject Matter under 35 U.S.C. § 101," filed Jun. 2, 2016, in United States International Trade Commission, Washington, D.C. (Investigation No. 337-TA-973) [in the Matter of Certain Wearable Activity Tracking Devices, Systems, and Components Thereof].
Litigation Document—"Complainant's Petition for Review of the Initial Determination Granting Summary Determination that the Asserted Patents are Directed to Ineligible Subject Matter under 35 U.S.C. § 101," filed Aug. 1, 2016, in United States International Trade Commission, Washington, D.C. (Investigation No. 337-TA-973) [in the Matter of Certain Wearable Activity Tracking Devices, Systems, and Components Thereof].
Litigation Document—"Summary Pursuant to 19 C.F.R. § 210.43(b)(2) of Complainant's Petition for Review of the Initial Determination Granting Summary Determination that the Asserted Patents are Directed to Ineligible Subject Matter under 35 U.S.C. § 101," filed Aug. 1, 2016, in United States International Trade Commission, Washington, D.C. (Investigation No. 337-TA-973) [in the Matter of Certain Wearable Activity Tracking Devices, Systems, and Components Thereof].
Litigation Document—"Notice of Commission Determination to Review an Initial Determination Granting Respondents' Motion for Summary Determination that Certain Asserted Claims are Directed to Ineligible Subject Matter under 35 U.S.C. § 101; and on Review to Remand the Investigation to the Presiding Administrative Law Judge," issued Sep. 7, 2016, in United States International Trade Commission, Washington, D.C. (Investigation No. 337-TA-973) [in the Matter of Certain Wearable Activity Tracking Devices, Systems, and Components Thereof].
U.S. Appl. No. 61/736,310, filed Dec. 12, 2012, William Ahmed et al., entitled "Fitness Monitoring Systems and Methods Based on Continuous Collection of Physiological Data," 61pp [Exhibit 4].
U.S. Appl. No. 61/696,525, filed Sep. 4, 2012, William Ahmed et al., entitled "Fitness Monitoring Systems and Methods Based on Continuous Collection of Physiological Data," 47pp [Exhibit 5].
Gasparrini et al. (2013) "Evaluation and Possible Improvements of the ANT Protocol for Home Heart Monitoring Applications," *IEEE*, 978-J1-4673-2874-6/13, 7pp [Exhibit 6].
"UP3 ™, the world's most advanced tracker," (Oct. 14, 2015) *Jawbone*, 10pp [Exhibit 12].
"UP4™, a fitness tracker so advanced it pays," (Oct. 14, 2015) *Jawbone*, 12pp [Exhibit 13].
"User's Guide, MIO Drive+ Petite," User's guide and how-to videos available at www.mioglobal.com, 3pp [Exhibit 16].
"Solo 915, Heart Rate + Calorie Monitor," (2009) *Sportline®*, [retrieved on Oct. 15, 2010 at www.sportline.com] 25pp [Exhibit 17].
U.S. Notice of Allowance dated Oct. 14, 2014 issued in U.S. Appl. No. No. 14/295,144, 5pp [Exhibit 18].
"Health Touch™ Plus User Guide," (2011) *Timex Group USA, Inc.*, 12pp [Exhibit 18].
Czarnul, Pawel (Jun. 6-8, 2013) "Design of a Distributed System using Mobile Devices and Workflow Management for Measurement and Control of a Smart Home and Health," Sopot, Poland, *IEEE*, pp. 184-192, 10pp [Exhibit 19].
Rabinovich, Roberto A., and Louvaris, Zafeiris et al. (Feb. 8, 2013) "Validity of Physical Activity Monitors During Daily Life in Patients With COPD," *ERJ Express, European Respiratory Society*, 28pp [Exhibit 24].
Horvath et al. (2007) "The effect of pedometer position and normal gait asymmetry on step count accuracy," *Appl. Physiol. Nutr. Metab.*, 32:409-415, 8pp [Exhibit 32].
Graser et al. (2007) "Effects of Placement, Attachment, and Weight Classification on Pedometer Accuracy," *Journal of Physical Activity and Health*, 4(4):359-369, 13pp [Exhibit 33].
Vyas et al. (2012) "Machine Learning and Sensor Fusion for Estimating Continuous Energy Expenditure," *AI Magazine*, pp. 55-61, 13pp [Exhibit 42].
"New Lifestyles, NL-800 Activity Monitor, User's guide & record book," (2005), New Lifestyles, Inc., 37pp.
"StepWatch Step Activity Monitor, U.S. Pat. No. 5,485,402," (2001) StepWatch™, *Prosthetics Research Study*, 7pp.
Litigation Document—"Plaintiffs Original Complaint for Patent Infringement," filed Jan. 4, 2016, in U.S. District Court for the

(56) References Cited

OTHER PUBLICATIONS

Eastern District of North Carolina (Court Docket No. 5:16-cv-00002-Fl) [Re: U.S. Pat. Nos. 8,923,941, 8,886,269, 8,929,965 and 8,989,830], 11 pp.
Cooper, Daniel (Aug. 16, 2013) Withings Pulse review, http://www.engadget.com/2013/08/16/withings-pulse-revew/, 8 pages.
Dunn et al. (2007) "A Novel Ring Shaped Photodiode for Reflectance Pulse Oximetry in Wireless Applications," IEEE Sensors Conference, pp. 596-599.
Kim, D. et al. A Linear Transformation Approach for Estimating Pulse Arrival Time. Journal of Applied Mathematics. vol. 2012. Jan. 20, 2012. [Retrieve Jun. 19, 2017]. Retrieved from internet: <https://www.emis.de/journals/HOA/JAM/Volume2012/643653.pdf> pp. 1-12.
Lifetrnr, User Manual (2003, specific date unknown), Nb new balance®, Implus Footcare, LLC, 3 pages.
Rainmaker, (Jun. 25, 2012, updated Feb 16, 2013) "Garmin Swim watch In-Depth Review," [retrieved on Sep. 9, 2013 at http://www.dcrainmaker.com/2012/06/garmin-swim-in-depth-review.html, 38 pp.
"Withings pulse, Quick Installation Guide" (Jul. 24, 2013) Withings Pulse QIG, v 1.3, withings.com/pulse, 16 pages.
Zijlstra, Wiebren, (2004) "Assessment of spatio-temporal parameters during unconstrained walking," *Eur J Appl Physiol*, 92:39-44.
Garmin Forerunner® 410 Gps-Enabled Sports Watch with Wireless Sync Owner's Manual, 52 pages.
Rainmaker, "Basis B1 Watch In-Depth Review", Jul. 2013, http://www.dcrainmaker.com/2013/07/basis-b1-review.html, 56 pages.
Polar Wearlink® + Coded Transmitter 31 Coded Transmitter W.I.N.D. User Manual, Polar, 11 pages.
Jawbone UP Band, "Parts of your Band", 1 page.
Nike+ SportWatch GPS User Guide, 42 pages.
Nike+ SportBand User's Guide, 36 pages.
Nike+ FuelBand User's Guide, 26 pages.
Lark/Larkpro User Manual 7 pages.
Larklife User Manual, 7 pages.
Garmin Swim Owner's Manual, 12 pages.
Forerunner® 910XT Owner's Manual, 56 pages.
Garmin Forerunner® 405 GPS-Enabled Sports Watch with Wireless Sync, 56 pages.
Garmin Forenmner® 310XT Multisport GPS Training Device, 56 pages.
Garmin Forenmner®' 10 Owner's Manual, 10 pages.
Garmin Forenmner® 410 GPS-Enabled Sports Watch with Wireless Sync Owner's Manual, 52 pages.
Gannin Forerunner® 210 GPS-Enable Sports Watch Owner's Manual, 28 pages.
Garmin Forenmner® 110 GPS-Enabled Sports Watch, 16 pages.
Garmin Forerunner® 405CX GPS-Enabled Sports Watch with Wireless Sync Owner's Manual, 56 pages.
Gannin Forerunner® 205/305 Owner's Manual. 80 pages.
Gannin Forerunner® 50 with ANT+Sport™ Wireless Technology Owner's Manual, 44 pages.
Garmin Forenmner® 301 Personal Trainer Owner's Manual. 66 pages.
Garmin Forenmner® 201 Personal Trainer Owner's Manual. 48 pages.
Fitbit User's Manual, Oct. 22, 2009, 15 pages.
Empson, "Basis Reveals an Awesome New Affordable Heart and Health Tracker You can Wear on Your Wrist", Sep. 22, 2011, https://techcnmch.com/2011/09/22/basis-reveals-an-awesome-new-affordable-heart-and-health-tracker-you-can-wear-on-your-wrist/, 3 pages.
DesMarais, "Which New Activity Tracker is Best for You?" Sep. 3, 2013, Health and Home, Health & Fitness, Guides & Review's, http://www.techlicious.com/guide/which-new-activity-tracker-is-right-for-you/,4 pages.
Chudnow, "Basis Wristband Make Its Debut", The Wired Self, http://thewiredself.com/health/basis-wrist-band-make-its-debut/, 3 pages.
"Activator for iPhone", IPhone-Tips-And-Advice.com, Jul. 9, 2013, http://www.iphone-tips-and-advice.com/activator.html, 10 pages.

\* cited by examiner

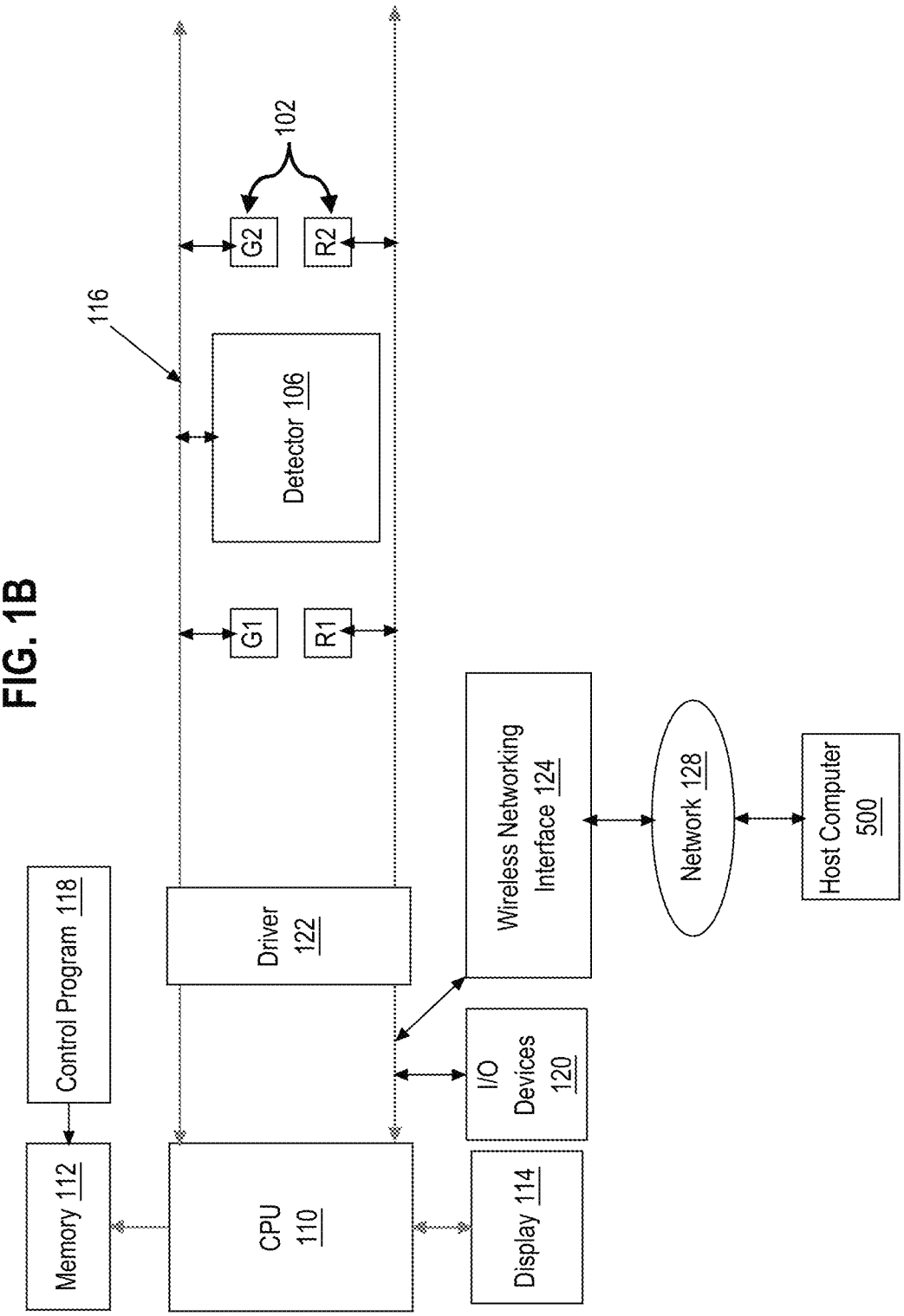

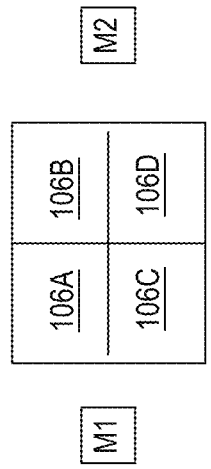
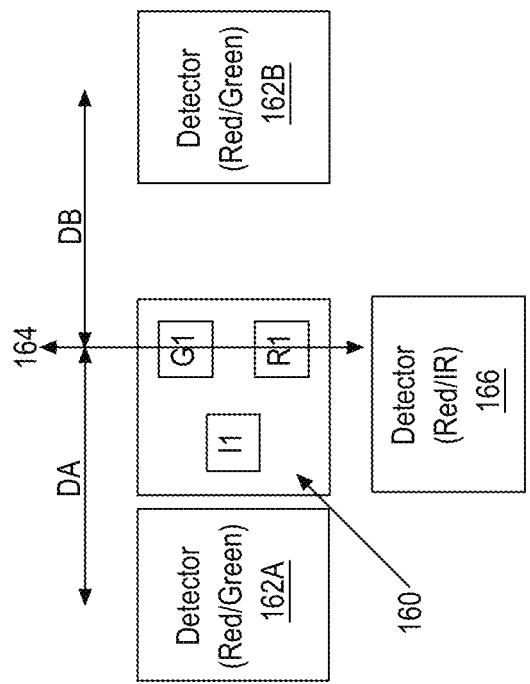
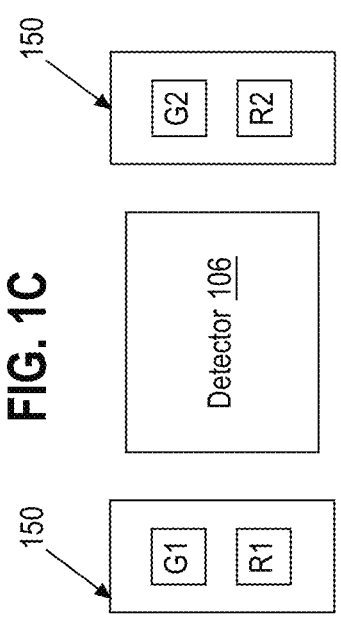
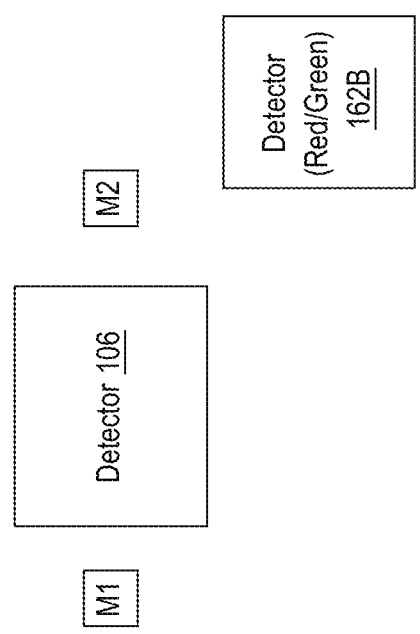

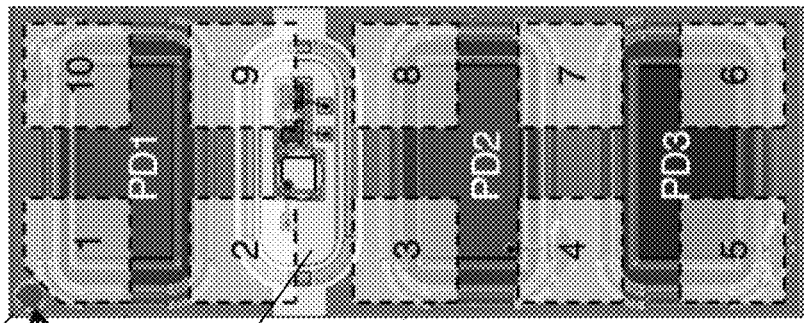
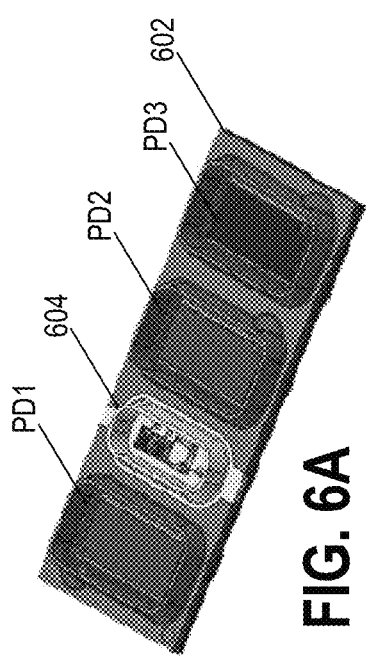
FIG. 6A
FIG. 6B
FIG. 6C
| Pin | Name | Function |
|---|---|---|
| 1 | PD1_A | Photodiode 1 Anode |
| 2 | G_C | Green LED Cathode |
| 3 | IR_C | IR LED Cathode |
| 4 | PD2_A | Photodiode 2 Anode |
| 5 | PD3_A | Photodiode 3 Anode |
| 6 | PD3_C | Photodiode 3 Cathode |
| 7 | PD2_C | Photodiode 2 Cathode |
| 8 | R_C | Red LED Cathode |
| 9 | G-R-IR_A | Green, Red, Infrared Anode |
| 10 | PD1_C | Photodiode 1 Cathode |

MULTI-CHANNEL PHOTOPLETHYSMOGRAPHY SENSOR

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

FIELD OF THE DISCLOSURE

The present disclosure generally relates to techniques for using one set of photoplethysmography (PPG) signals to improve a heart rate measurement that has been determined based upon a second set of PPG signals.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

A photoplethysmography (PPG) sensor may be utilized to detect the volumetric change in blood vessels. A PPG sensor usually consists of a light source, typically a light-emitting diode (LED), and a light-sensitive sensor, typically a photodiode. Blood which passes between the light source and sensor will modulate a characteristics of the tissue along the light path between the two, resulting in a detectible deviation in the current produced by the photodiode. From this signal and applying various algorithms, a heart rate estimate can be determined.

Typical PPG technologies rely on emitting a single wavelength of green, red or infra-red (IR) light from an LED. Many wearable PPG devices use green light, as with green light the hemoglobin absorption of light is up to 20 times greater at green wavelengths than at IR wavelengths. However, red or IR light devices may be more efficient and use less power, and photodiodes tuned to these wavelengths may be more responsive. PPG technology suffers from severely reduced accuracy when the user is performing high-motion activities or certain activities which contort the wrist and thus affect the dynamics of blood flow within the wrist. The received light is modulated by these movements at an order of magnitude much greater than the desired cardiac signal. Low signal quality in PPG signals also can be caused by characteristics of the local area that is sensed. For instance, signal quality can vary greatly even if a wrist-worn PPG sensor is moved only a few millimeters up or down the wrist or signal quality can also vary due to variations in the wavelength being emitted. In addition, during motion, certain orientations of wrist-worn PPG devices are subject to more motion and, therefore, greater degradation of the PPG signal due to such motion.

SUMMARY

The appended claims may serve as a summary of the disclosure.

BRIEF DESCRIPTION OF THE DRAWINGS

In the drawings:

FIG. 1B illustrates an example hardware architecture of the monitoring device of FIG. 1A, FIG. 2 and showing a first example arrangement of light sources and a detector.

FIG. 1C illustrates a portion of FIG. 1A, FIG. 1B having a second example arrangement of light sources and a detector.

FIG. 1D illustrates a portion of FIG. 1A, FIG. 1B having a third example arrangement of light sources and a detector.

FIG. 1E illustrates a portion of FIG. 1A, FIG. 1B having a fourth example arrangement of light sources and a detector comprising a plurality of discrete detectors.

FIG. 1F illustrates a portion of FIG. 1A, FIG. 1B having a fifth example arrangement of light sources and a plurality of discrete detectors.

FIG. 6A is a perspective view of a sixth example arrangement of light sources and a plurality of discrete detectors.

FIG. 6B is a top plan view of the arrangement of FIG. 6A showing locations of pins to electrically couple the arrangement to other devices.

FIG. 6C illustrates example pin assignments of the pins of FIG. 6B.

DETAILED DESCRIPTION

Figure 1A:
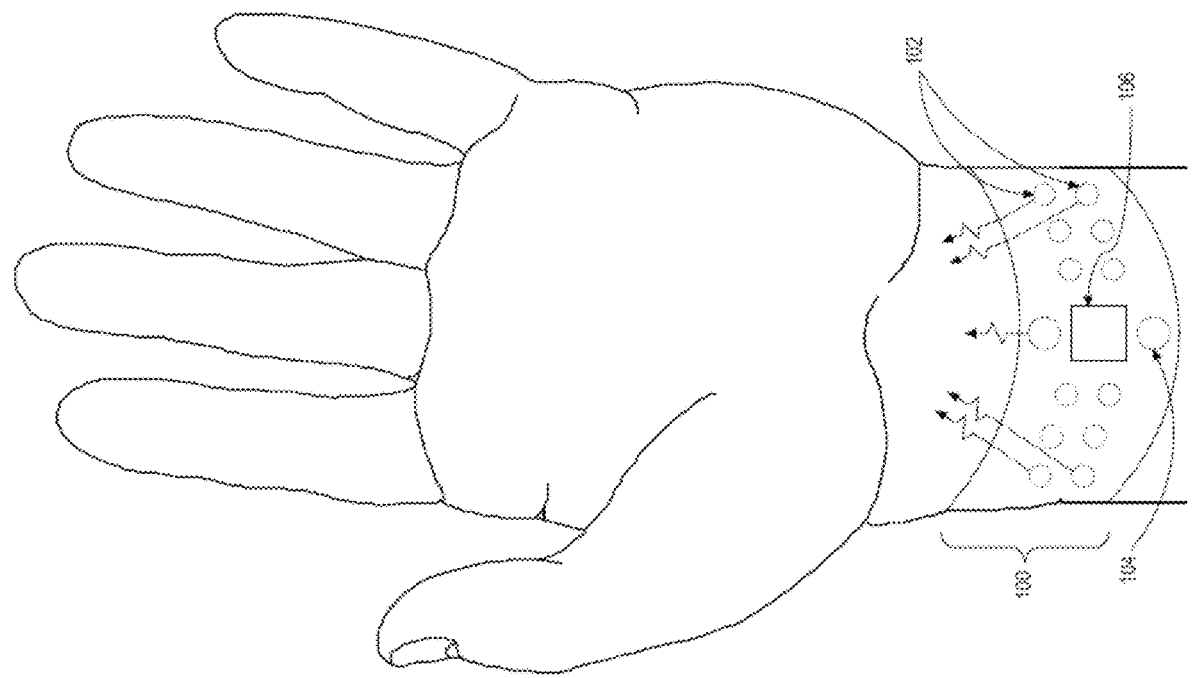
FIG. 1A illustrates a monitoring device worn by a user, in accordance with one example.

In the following description, for the purposes of explanation, numerous specific details are set forth in order to provide a thorough understanding of the present disclosure. It will be apparent, however, that embodiments may be practiced without these specific details. In other instances, well-known structures and devices are shown in block diagram form in order to avoid unnecessarily obscuring the present disclosure. Embodiments are described according to the following outline:

1. GENERAL OVERVIEW
2. EXAMPLE MONITORING DEVICE
2.1 FIRST EXAMPLE ARRANGEMENT OF LIGHT SOURCES
2.2 OTHER EXAMPLE ARRANGEMENTS OF LIGHT SOURCES
3. EXAMPLE HEART RATE ESTIMATION TECHNIQUES
4. IMPLEMENTATION EXAMPLE-HARDWARE OVERVIEW

1. General Overview

In one embodiment, a data processing method comprises obtaining one or more first photoplethysmography (PPG) signals based on one or more first light sources that are configured to emit light having a first light wavelength; obtaining one or more second PPG signals based on one or more second light sources that are configured to emit light having a second light wavelength; generating an estimated heart rate value based on one or more of the first PPG signals and the second PPG signals; and causing the estimated heart rate value to be displayed via a user interface on a client device.

In an embodiment, a data processing method comprises obtaining one or more first photoplethysmography (PPG) signals based on one or more first light sources that are configured to emit light having a first light wavelength corresponding to a green light wavelength; obtaining one or more second PPG signals based on one or more second light sources that are configured to emit light having a second light wavelength corresponding to a red light wavelength, one or more of the first light sources and one or more of the second light sources being co-located; generating an estimated heart rate value based on one or more of the first PPG signals and the second PPG signals; and causing the estimated heart rate value to be displayed via a user interface on a client device.

In another embodiment, an activity monitoring apparatus comprises one or more processors; a non-transitory computer-readable storage medium coupled to the one or more processors and storing one or more sequences of instructions which, when executed using the one or more processors, cause the one or more processors to perform: obtaining one or more first photoplethysmography (PPG) signals based on one or more first light sources that are configured to emit light having a first light wavelength corresponding to a green light wavelength; obtaining one or more second PPG signals based on one or more second light sources that are configured to emit light having a second light wavelength corresponding to a red light wavelength, one or more of the first light sources and one or more of the second light sources being co-located; generating an estimated heart rate value based on one or more of the first PPG signals and the second PPG signals; and causing the estimated heart rate value to be displayed via a user interface on a client device.

In yet another embodiment, a data processing method comprises obtaining one or more first photoplethysmography (PPG) signals based on one or more first light sources that are configured to emit light having a green light wavelength; obtaining one or more second PPG signals based on one or more second light sources that are configured to emit light having a red light wavelength or an infrared wavelength; generating an estimated heart rate value based on one or more of the first PPG signals and the second PPG signals, the generating comprising: identifying motion signals in the one or more second PPG signals; removing corresponding motion signals from the first PPG signals to generate modified first PPG signals; and generating the estimated heart rate value based on the modified first PPG signals; and causing the estimated heart rate value to be displayed via a user interface on a client device.

In still another embodiment, an activity monitoring apparatus comprises one or more processors; a non-transitory computer-readable storage medium coupled to the one or more processors and storing one or more sequences of instructions which, when executed using the one or more processors, cause the one or more processors to perform: obtaining one or more first photoplethysmography (PPG) signals based on one or more first light sources that are configured to emit light having a green light wavelength; obtaining one or more second PPG signals based on one or more second light sources that are configured to emit light having a red light wavelength or an infrared wavelength; generating an estimated heart rate value based on one or more of the first PPG signals and the second PPG signals, the generating comprising: identifying motion signals in the one or more second PPG signals; removing corresponding motion signals from the first PPG signals to generate modified first PPG signals; and generating the estimated heart rate value based on the modified first PPG signals; and causing the estimated heart rate value to be displayed via a user interface on a client device.

Various other aspects and features of different embodiments will become apparent from the description, drawings and claims.

For purposes of this disclosure, the term "light path" is used to describe the probabilistic path of photons from one location to another, typically from the light emitter to the light detector. Photons emitted by the light emitter will follow many different paths to the detector. For simplicity and clarity, the path that results from the optical power-weighted average of all the possible paths is described simply as the "light path" in some embodiments. In some alternative embodiments, "light path" refers to the path along which most of the photons travel.

2. Example Monitoring Device

Embodiments provide PPG-based devices that are configured to use a first light source to detect a cardiac signal and a second light source to improve the signal quality obtained from the first light source, especially during high-motion activities. The specific number, arrangement and position of the light sources, and detectors that detect light emitted by the light sources, may vary in different embodiments as further described herein.

2.1 First Example Arrangement of Light Sources

FIG. 1A illustrates a monitoring device worn by a user, in accordance with one example. FIG. 1B illustrates an example hardware architecture of the monitoring device of FIG. 1A and/or FIG. 2 and showing a first example arrangement of light sources and a detector. For purposes of illustrating a clear example, FIG. 1A and other aspects of this disclosure describe a monitoring device that is configured for wearing on the wrist, but other embodiments may be implemented using monitoring devices that are wearable in other anatomical locations such as the ear, head, fingertips, ankle, neck, upper arm, torso, leg and/or forehead (such that light sources of the monitoring devices are configured to be aligned adjacent to blood vessels of a human, as described in more detail).

Figure 2:
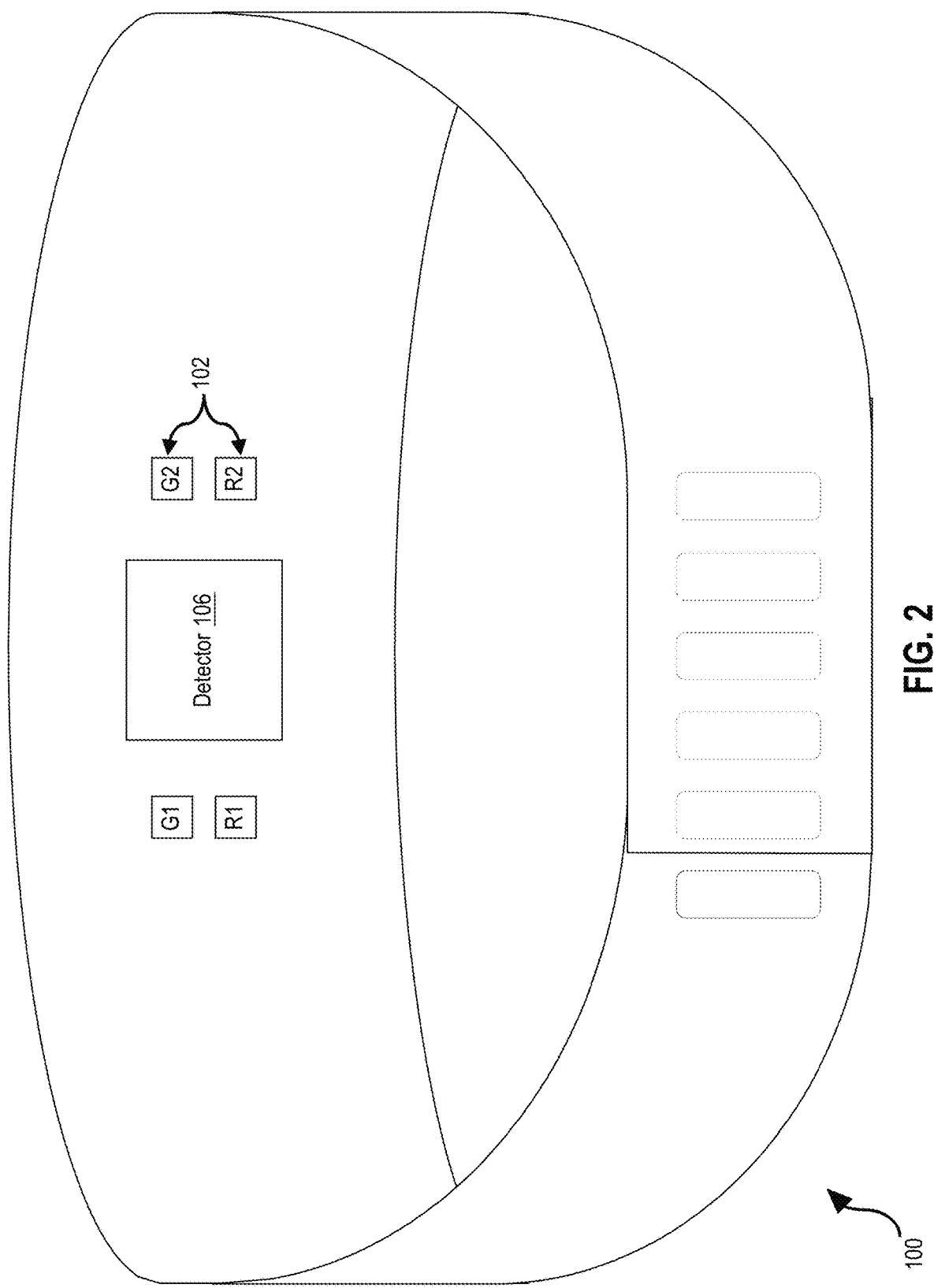
FIG. 2 illustrates a perspective view of a monitoring device, in accordance with one example.

The arrangement of FIG. 1A, FIG. 1B, and FIG. 2, implement a first strategy for improving heart rate estimates based upon PPG signals, using co-located emitters of multiple wavelengths of light that have different rates of absorption, reflectance, and/or scattering in response to interaction with hemoglobin, or different rates of absorption, reflectance, and/or scattering in response to interaction with melanin. As described further in other sections herein, first PPG signals obtained from first light sources using a first light wavelength, and second PPG signals obtained from second light sources using a second light wavelength, can be used to identify motion and cardiac components of the PPG signals. The first and second PPG signals and second PPG signals may be obtained simultaneously (e.g., where the first light sources and second light sources are simultaneously active). In these embodiments the first PPG signals could be any wavelength that has been determined or known to have a relatively greater cardiac component, and the second PPG signals could be any wavelength that has been determined or known to have a relatively greater motion component. In one embodiment, the first PPG signals are obtained from a green light source and the second PPG signals are obtained from a red or infrared light source. Furthermore, the multiple wavelengths of light also have different melanin responses, which can result in a difference of signal quality for the two wavelengths. Recognizing these components can facilitate a process in which, for example, motion components indicated in a second signal are removed from a first signal, thereby causing the first signal to more accurately represent cardiac activity of the user. However, the first strategy is merely one example and other strategies are possible, as now described.

A second strategy, which can be used in conjunction with the first, is to use multiple emitters of the same wavelength at different locations such that light paths are different from each of the different emitters to a given detector. Thus a first light wavelength from a first light source may correspond to a second light wavelength from a second light source, and the first light sources and the second light sources are at different locations having different light paths with respect to one or more detectors. "Light path," in some embodiments, may refer to an approximated vector having an origin at a center of a light source and terminating anywhere in the surface area of a detector, and representing an approximate path of light from source to detector. The second strategy may be combined with the first strategy, such that the second light wavelength may be different from the first light wavelength, and the first light sources and the second light sources may be at different locations having different light paths with respect to one or more detectors.

A third strategy, which can be used in conjunction with the first and/or second, or both the first and second, is to use a plurality of discrete detectors such that the light paths from the emitters are different at each detector location. In this strategy, at least one of the first PPG signals or at least one of the second PPG signals may be obtained using a first detector, at least one of the first PPG signals or at least one of the second PPG signals may be obtained using a second detector, and the first detector and the second detector are located at different locations having different light paths with respect to one or more of the first light sources and with respect to one or more of the second light sources.

The PPG signals corresponding to these multiple paths and/or multiple wavelengths are then compared using a quality metric such as signal-to-noise ratio (SNR) and the highest quality can be selected to be used for estimating heart rate.

In one embodiment, two light sources emit at two different wavelengths, and the two light sources are spatially located as close as possible. For example, in the arrangement of FIG. 1A, FIG. 1B, and FIG. 2, the light sources are co-located. The term "co-located," in this disclosure, means positioned with minimal distance between the lights sources (e.g., of different wavelengths), so that the detector senses light emitted by the different light sources that interacts with the same tissue or approximately the same tissue. In some embodiments, co-location may refer to emitters that are located within a predetermined distance of each other. In some embodiments, the predetermined distance is less than 1 mm, and in some embodiments, the predetermined distance is within the range of 0.3 mm-0.9 mm.

In one implementation, two discrete LED emitters are co-located or assembled close to one another. In another implementation, both a green light source and red light source may be in the same light source package, which may comprise the same lens and/or the same die. Another implementation uses one or more red-green-blue (RGB) LEDs containing these three dies (red, green, and blue) in the same package. Another implementation uses one or more red-green-infrared LEDs containing these three dies (red, green, and infrared) in the same package. Using different light sources that are co-located allows the detector 106 to sense close to the same light path for each wavelength of light.

In one embodiment, independent control of all light sources is provided. In other embodiments, several light sources are controlled together as a gang or bank; for example, all green light sources are controlled in one bank and all red light sources are controlled in another bank. A benefit of independent control of each light source, or independent readout from each of multiple detectors (e.g., obtaining independent signals based on the same or different light wavelengths from each of multiple detectors), is that a multiple light path approach may be used to improve the HR estimation, as discussed further in other sections herein.

In an embodiment, a monitoring device 100 comprises one or more light sources 102 (e.g., one or more pairs of light sources 102), one or more additional light sources 104 (e.g., one or more pairs of additional light sources 104), and one or more detectors 106. In some embodiments, additional light sources 104 may be omitted, and each light source 102 (or each light source in a pair of the light sources 102) may use a different light wavelength, as discussed further herein. For purposes of illustrating a clear example, FIG. 1A depicts light sources 102, additional light sources 104, and detectors 106 in an enlarged form, and in practical embodiments, these elements may be implemented using miniature components that are smaller than shown in FIG. 1A. In practice, the light sources 102 and additional light sources 104 are positioned to permit the detector 106 to detect reflected light that is emitted from the light sources toward the skin and therefore the light sources and detector may be closely located on a miniature substrate within a housing, band or other protective elements of the monitoring device 100.

As seen in FIG. 1B, the monitoring device 100 may further comprise a central processing unit (CPU) 110 coupled to a memory 112, display 114, bus 116, one or more input/output (I/O) devices 120, and a wireless networking interface 124. Display 114 and/or I/O devices 120 may be omitted in certain embodiments. Display 114 may comprise a liquid crystal display, light-emitting diode display, touchscreen, or other electronic digital display device that a CPU can drive. Display 114 may be programmed or configured to display data, such as time, heart rate, and blood oxygen saturation (SpO$_2$) levels of a user. In an embodiment, the monitoring device 100 is a wristband and the display 114 is configured such that the display faces away from the outside of a user's wrist when the user wears the monitoring device. In other embodiments, the display 114 may be omitted and data detected by the monitoring device 100 may be transmitted using the wireless networking interface 124 via near-field communication (NFC), BLUETOOTH, WiFi, or other suitable wireless communication protocols to a host computer 500 for analysis, display and/or reporting.

I/O devices 120 may include, for example, motion sensors, vibration devices, lights, loudspeakers or sound devices, microphones, or other analog or digital input or output devices. Memory 112 may comprise RAM, ROM, FLASH memory or other digital data storage, and may include a control program 118 comprising sequences of instructions which when loaded from the memory and executed using the CPU 110 cause the CPU to perform the functions that are described herein. The light sources 102, additional light sources 104, and detectors 106 may be coupled to bus 116 directly or indirectly using driver circuitry by which the CPU may drive the light sources and obtain signals from the detectors.

The host computer 500 may be coupled to the wireless networking interface 124 via one or more networks 128, which may include one or more local area networks, wide area networks, and/or internetworks using any of terrestrial or satellite links. In some embodiments, host computer 500 executes control programs and/or application programs that are configured to perform some of the functions described herein including but not limited to the processes described herein with respect to FIG. 3, FIG. 4A, and FIG. 4B.

Bus 116 may be coupled to light sources 102 and detector 106 in any of several arrangements or geometries as further described herein. In one example arrangement, the light sources 102 comprise a first pair of light sources G1, R1 and a second pair of light sources G2, R2. Each pair may comprise a first light source associated with a first light wavelength and a second light source associated with a second, different wavelength. For example, G1, G2 may comprise light sources that use the same first wavelength, and R1, R2 may use a second, different wavelength. In one arrangement, G1, G2 emit light in a green visible light wavelength and R1, R2 emit light in a red visible light wavelength. Light sources using other wavelengths such as infrared may be used in other arrangements, in place of either G1, G2 or R1, R2.

Referring again to FIG. 1A, for purposes of illustrating a clear example, FIG. 1A depicts six pairs of light sources 102, two additional light sources 104, and one detector 106, but in other embodiments the monitoring device 100 may contain any number of light sources 102 (e.g., pairs of light sources 102), additional light sources 104, and detectors 106. In an embodiment, light sources 102, additional light sources 104, and detectors 106 are configured to be aligned proximate to a user's skin when monitoring device 100 is worn. "Proximate" may mean any of slightly separated from, near, adjacent to, or in direct contact with, but direct contact is not required. For example, in FIG. 1A, monitoring device 100 is worn on the wrist of a user such that light sources 102, additional light sources 104, and detectors 106 are adjacent to the inner wrist of the user. The positioning of the monitoring device 100 as shown in FIG. 1A is provided merely as an example, and other embodiments may use alternative positioning. For example, the device may be positioned where light sources 102, additional light sources 104, and detectors 106 are oriented on the outer wrist rather than the inner wrist. The monitoring device 100 may be formed with perimeter dimensions of different sizes that cause the light sources 102, additional light sources 104, and detectors 106 to be in contact with the skin, or separated from the skin.

FIG. 2 illustrates a schematic perspective view of a monitoring device in one embodiment. As an example, FIG. 2 has the arrangement of light sources and detector of FIG. 1B. In this embodiment, monitoring device 100 comprises a wrist band in which light sources 102 and detector 106 are mounted on or within an underside of monitoring device 100. Monitoring device 100 may include a fastening means to attach monitoring device to a portion of a user's body and the specific form of the fastening means is not critical. The fastening means may be a strap that is passed through a receiving portion of the strap and fastened with hook and/or loop fasteners. Other fastening means may include clips, latches, hook-and-loop fasteners such as VELCRO, clasps, ties, and/or adhesives. The fastening means may be located on any side of monitoring device 100 such that the fastening device does not interfere with movement or activity.

In an embodiment, the monitoring device 100 may comprise a processor, memory, user interface, wireless transceiver, one or more environmental sensors, and one or more biometric sensors other than the detector 106. For example, embodiments may be implemented using a monitoring device of the type shown in U.S. Pat. No. 8,948,832 of Fitbit, Inc., San Francisco, Calif., the entire contents of which are hereby incorporated by reference for all purposes as if fully set forth herein. In other words, the monitoring device of the type shown in U.S. Pat. No. 8,948,832 could be modified based upon the additional disclosure herein to result in a working activity monitoring apparatus capable of performing the functions that are described herein. Therefore, the present disclosure presumes that the reader knows and understands U.S. Pat. No. 8,948,832, and this disclosure is directed to persons having a level of skill sufficient to modify or adapt the monitoring device of the type shown in U.S. Pat. No. 8,948,832 based upon the additional disclosure herein to result in a working activity monitoring apparatus capable of performing the functions that are described herein.

In various embodiments, the light sources 102 comprise electronic semiconductor light sources, such as light-emitting diodes (LEDs), or produce light using any of filaments, phosphors, or laser. The first light sources and the second light sources may comprise two LED emitters that are co-located, either in separate packages or dies or in a single package or die.

In any of the embodiments herein, the detector 106 may comprise any of a photodiode, phototransistor, charge-coupled device (CCD), thermopile detector, or complementary metal-oxide-semiconductor (CMOS) sensor. The detector 106 may comprise multiple detector elements, as further described herein. One or more of the detectors may comprise a bandpass filter circuit.

In an embodiment, each pair of light sources 102 includes a red light source denoted R1, R2 and a green light source denoted G1, G2. The light sources R1, R2 may emit light with peak wavelengths typically in the range of 550 nm to 940 nm. For example, in various embodiments a particular red light source may emit light with a peak wavelength of 560 nm.

In an embodiment, light sources G1, G2 may be configured to emit light with wavelengths in the range of 495 nm to 570 nm. For example, a particular green light source may emit light with a wavelength of 528 nm.

In some embodiments, R1, R2 may comprise infrared light sources that may emit light with peak wavelengths in the range of 750 nm to 1700 nm. By way of example and not limitation, a particular infrared light source may emit light with a peak wavelength of 730 nm, 760 nm, 850 nm, 870 nm, or 940 nm. Commercial light sources such as LEDs tend to provide output at about 20 nm intervals with a center wavelength tolerance of +/−10 nm from the manufacturer's specified wavelength and thus one possible range of useful peak wavelengths for the light sources is 550 nm to 950 nm.

In an embodiment, the light sources 102 are mounted in positions that are spaced apart along a substrate. In an embodiment, the light sources 102 may be laterally aligned on a substrate with detectors 106. For example, FIG. 1A and FIG. 2 depict two pairs of light sources 102 on either side of detector 106. Pairs of light sources on one side of a detector 106 may be equally spaced from detectors 106 as corresponding pairs on an opposite side of the detector. Additionally and/or alternatively, pairs of light sources may be equally spaced from each other. For example, on one side of detector 106, a first pair of light sources R1, G1 may be placed 1 mm from the detectors and a second pair of light sources R2, G2 may be placed 1 mm from the first light sources. Other pairs with similar spacing may be used.

The spacing of the light sources may be measured from the side of the light source or the center of the light source. For example, the light sources may be configured such that the center of each light source of a first pair of light sources is 2 mm from the edge of detector 106 and the center of each light source of a second pair of light sources is 2 mm from the center of a corresponding light source in the first pair of light sources. The particular magnitude of the spacing may depend on a number of factors and this disclosure does not limit the embodiments to any particular spacing. For example, spacing in a range of 1 mm (or less) to 10 mm would be workable in various embodiments.

The orientation of the light sources on either side of detector 106 may be the same. For example, in the orientation depicted in FIG. 2, each pair of light sources may comprise a top light source comprising a green LED and a bottom light source comprising a red LED. In other embodiments, light sources on either side of detector 106 may have opposite orientations. Additionally and/or alternatively, light sources on one side of detector 106 may have different orientations. For example, a first pair of light sources on one side of detector 106 may comprise a top light source comprising a red LED and a second pair of light sources on the other side of detector 106 may comprise a top light source comprising a green LED.

Further, in some embodiments, one or more of the light sources 102 may comprise a single LED package that emits multiple wavelengths, such as green, red and/or infrared wavelengths, at the same location with respect to multiple detectors. Such LEDs may include multiple semiconductor elements that are fabricated using a single die in a single packages, and therefore FIG. 1, FIG. 2 are not intended to imply that separate components in separate packages are required.

Detector 106 is one or more sensors that is/are adapted to detect wavelengths of light emitted from light sources 102. A particular light source 102 combined with a particular detector 106 may comprise a sensor such as a PPG sensor. A first PPG sensor and a second PPG sensor can share components, such as the same light sources and/or detectors, or have different components and thus the term "PPG sensor" is used for simplicity of description although actual embodiments may use multiple components in implementing a PPG sensor. Detector 106, in an embodiment, may comprise one or more detectors for detecting each different wavelength of light that is used by the light sources. For example, a first detector may be configured to detect light with a wavelength of 560 nm, a second detector may be configured to detect light with a wavelength of 940 nm, and a third detector may be configured to detect light with a wavelength of 528 nm. Examples include photodiodes fabricated from semiconductor materials and having optical filters that admit only light of a particular wavelength or range of wavelengths.

In other embodiments, detector 106 comprises one or more detectors configured to detect multiple wavelengths of light. For example, a single detector may be configured to tune to different frequencies based on data received from an electrical digital microprocessor coupled to detectors 106. In another way, the single detector may include multiple active areas where each active area is sensitive to a given range of wavelengths. In an embodiment, a single detector is configured to detect light with wavelengths in the red and infrared frequencies and a second detector is configured to detect light with wavelengths in the green frequencies. Further, each of the light sources 102 and additional light sources 104 may use any of one or more different wavelengths of light as previously described.

In an embodiment, detectors 106 are mounted in a housing with one or more filters that are configured to filter out wavelengths of light other than wavelengths emitted by light sources 102. For example, a first portion of the housing may be covered with a filter which removes ambient light other than light in wavelengths emitted by light sources 102. For example, signals from light sources 102 may be received at detector 106 through an ambient light filter that filters out an ambient light source that generates an ambient light with a wavelength that is different from the wavelength that is detected by the detector.

2.2 Other Example Arrangements of Light Sources

FIG. 1C illustrates a portion of FIG. 1A, FIG. 1B having a second example arrangement of light sources and a detector. FIG. 1D illustrates a portion of FIG. 1A, FIG. 1B having a third example arrangement of light sources and a detector. FIG. 1E illustrates a portion of FIG. 1A, FIG. 1B having a fourth example arrangement of light sources and a detector comprising a plurality of discrete detectors. FIG. 1F illustrates a portion of FIG. 1A, FIG. 1B having a fifth example arrangement of light sources and a detector comprising a plurality of discrete detectors.

Referring first to FIG. 1C, in one embodiment, a light-combiner or a diffusive layer 150 is provided over each pair of light sources G1, R1 and G2, R2. Layer 150 to combine and/or diffuse light emitted from different light sources, such as G1, R1, to reduce the dependence of the sensed signal upon a distance or position of the detector 106 with respect to the light sources G1, R1 and/or G2, R2.

As seen in FIG. 1D, in an embodiment, one or more multiple-die light source packages M1, M2 may be used, each of which includes two or more light sources using two or more different wavelengths in the same package. For example, each of M1, M2 may comprise RGB LEDs. As another example, each of M1, M2 may comprise red-green-infrared LEDs that emit red, green, and/or infrared light. In this arrangement, the spacing between different wavelength sources may be smaller than in the other arrangements previously described.

Referring now to FIG. 1E, in one embodiment, the detector comprises a plurality of detectors 106A, 106B, 106C, 106D within a detector region. Each of the detectors 106A, 106B, 106C, 106D forms a different light path with respect to light sources in multiple-die light source packages M1, M2. The arrangement of FIG. 1E also may be used with separate light sources R1, G1, R2, G2, as seen in FIG. 1A, FIG. 1B, and/or with a diffusion layer as seen in FIG. 1C.

Referring now to FIG. 1F, in an embodiment, a light source cluster 160 comprises a green spectrum light source G1, and a red spectrum light source R1. In an embodiment, the light sources G1, R1 are physically positioned between a first red-green spectrum light detector 162A and a second red-green spectrum light detector 162B. In one embodiment, the use of green and red light emission and detection in the arrangement of FIG. 1F has been found to be useful for heart rate detection. Dies for light sources G1, R1 are, in one embodiment, positioned as close as possible to one another and may be in a single module. Furthermore, in FIG. 1F, the first detector 162A is separated from a center axis 164 of alignment of light sources G1, R1 by a first distance DA. In an embodiment, the second detector 162B is separated from the center axis 164 by a second distance DB, which is equal to DA. Therefore, light paths between light sources G1, R1 and detectors 162A, 162B are the same.

In some embodiments, the light source cluster 160 is centered overall between detectors 162A, 162B, but a die in which the light sources G1, R1 are formed may be off center in the package, so that G1 and/or R1 are slightly closer to one detector than the other. Typically relatively little offset results, where offset is a fraction of the actual beam width that reaches the skin of the user after spreading out along the Z-axis height of the light source and housing.

Optionally, in another embodiment, an infrared light source I1 is positioned near the other light sources G1, R1; the proximity of I1 to G1, R1 facilitates manufacturing all of I1, G1, R1 as light-emitting diodes having a common anode connection. The infrared light source I1 is separated from at least one of the detectors 162A, 162B by a greater distance than the other detector. An additional detector 166 for infrared and red light may be positioned near the light source cluster 160 and away from the other detectors, in a position that will detect reflected light from at least detectors I1, R1. Therefore, in this embodiment a path between the light source I1 and its detector is different than paths between light sources R1, G1 and corresponding detectors; in the geometry shown in FIG. 1F the paths are effectively perpendicular. These optional elements may provide signals that are useful to assist with $CO_2$ measurements. Furthermore, an infrared signal from I1 also may be used to detect when the apparatus is removed from the body, and the apparatus may be programmed, in response to removal, to turn off the PPG module to conserve power since heart rate measurements cannot be made when the apparatus is not on a wrist or other body element. Off-body detection based on the IR signal, in this manner, may be performed alone or in combination with capacitive detection to indicate loss of skin contact.

FIG. 6A is a perspective view of a sixth example arrangement of light sources and a plurality of discrete detectors. FIG. 6B is a top plan view of the arrangement of FIG. 6A showing locations of pins to electrically couple the arrangement to other devices. FIG. 6C illustrates example pin assignments of the pins of FIG. 6B.

Referring first to FIG. 6A, in an embodiment, a light detection device 602 comprises a light source cluster 604 having green, red, and infrared light sources as further described in connection with FIG. 6B. Device 602 further comprises a plurality of detectors PD1, PD2, PD3 arranged in a linear row with at least one detector PD1 adjacent to a first side of the light source cluster 604 and the other detectors PD2, PD3 adjacent to a different, second side of the light source cluster.

From FIG. 6B it may be seen that the light source cluster 604 comprises green, infrared, and red light-emitting diodes, as viewed from left to right in FIG. 6B. The LEDs are structured with a common anode connection. Three (3) photodiode detectors for red light, infrared light and green light are positioned linearly in alignment with one another and the detectors for red light and infrared light are positioned closest to the light source cluster. In the nomenclature of FIG. 6B, PD1 and PD2 are photodiodes configured for red light and green light detection, and PD3 is a photodiode for red light and infrared light detection. For all of PD1, PD2, PD3, the frequency spectrum that is detected by each of them may be controlled by selection of an appropriate filter that is affixed over the photodiode semiconductor detection structures that comprise PD1, PD2, PD3. For example, in an embodiment, PD1 and PD2 may be configured with filters that attenuate most red light but pass some at a frequency on a border of the red spectrum, and pass all green light due to its typically weaker amplitude of reflection. Furthermore, in some embodiments PD3 detects all light frequencies and post-detection firmware or software filters are used to extract IR spectrum components and/or red spectrum components from the raw signal. FIG. 6C identifies pin numbers of electrical connection pins, pin names, and functions of the pin locations, in which pin numbers in FIG. 6C correspond to reference numerals that are superimposed over device locations in FIG. 6B.

In any of these embodiments, either independent control of all light sources may be provided, or several light sources are controlled together as a gang or bank; for example, all green light sources are controlled in one bank and all red light sources are controlled in another bank.

The configurations described in connection with FIG. 1A, FIG. 1B, FIG. 1C, FIG. 1D, FIG. 1E, FIG. 1F, FIG. 2 are merely exemplary, and it is understood that other configurations are possible. For example, while FIG. 1B and FIG. 2 shows a pair of emitters R1, G1 to the left of the detector 106 and another pair of emitters R2, G2 to the right of the detector 106, in some embodiments, a pair of emitters R1, G1 may be positioned on one side of the detector 106 (e.g., to the left of the detector 106) and no emitters may be positioned on the other side of the detector. As another example, in some embodiments, two detectors 106A and 106B may be positioned such that one detector is on either side of a pair of light sources 102 (such as a co-located pair of LEDs comprising one green LED and one red or infrared LED). As another example, in some embodiments, two detectors 106A and 106B may be positioned such that one detector is on either side of a single multiple-die light source package (e.g., a single red, and green, and infrared LED).

As described above, a light path represents an approximate path of light from a given source (or emitter) to a given detector. Thus, for example, if there are multiple emitters of the same or different wavelength such as R1, R2, G1, G2, etc., and multiple detectors such as detector 106A, detector 106B, etc., then distinct light paths exist between each of the multiple emitters and each of the multiple detectors, such as a light path from R1 to detector 106A, a light path from R2 to detector 106A, a light path from R1 to detector 106B, a light path from R2 to detector 106B, a light path from G1 to detector 106A, and so on. Moreover, in the case of a multiple-die LED (see FIG. 1D), each of the individual light sources in the single multiple-die LED (e.g., red, green, and infrared light sources) may be considered different emitters for the purposes of defining an emitter-detector light path. Thus, consistent with the embodiments described herein, PPG signals associated with any of the aforementioned light paths may be selectively obtained and utilized for estimating heart rate. For example, the PPG signals corresponding to any of multiple paths and/or multiple wavelengths may be compared using a quality metric such as signal-to-noise ratio (SNR) and the highest quality can be selected to be used for estimating heart rate.

3. Example Heart Rate Estimation Techniques

Certain flow diagrams are presented herein to illustrate various methods that may be performed by example embodiments. The flow diagrams illustrate example algorithms that may be programmed, using any suitable programming environment or language, to create machine code capable of execution by a CPU or microcontroller of the monitoring device 100. In other words, the flow diagrams, together with the written description in this document, are disclosures of algorithms for aspects of the claimed subject matter, presented at the same level of detail that is normally used for communication of this subject matter among skilled persons in the art to which the disclosure pertains. Various embodiments may be coded using assembly, C, OBJECTIVE-C, C++, JAVA, or other human-readable languages and then compiled, assembled, or otherwise transformed into machine code that can be loaded into ROM, EPROM, or other recordable memory of the activity monitoring apparatus that is coupled to the CPU or microcontroller and then then executed by the CPU or microcontroller.

For purposes of illustrating a clear example, this disclosure may describe the methods with reference to the devices/components shown in other figures, such as FIG. 1A, FIG. 1B, FIG. 1C, FIG. 1D, FIG. 1E, and FIG. 2. However, other embodiments may be implemented using data from other sources and computers or apparatus other than those shown in the aforementioned figures.

In an embodiment, PPG signals obtained from light sources having multiple wavelengths may be processed to filter or reject signal components that are associated with motion of the user, using a computer program to identify the motion component of the signal and remove it from the composite signal, leaving the cardiac component as a remainder or final signal.

Figure 3:
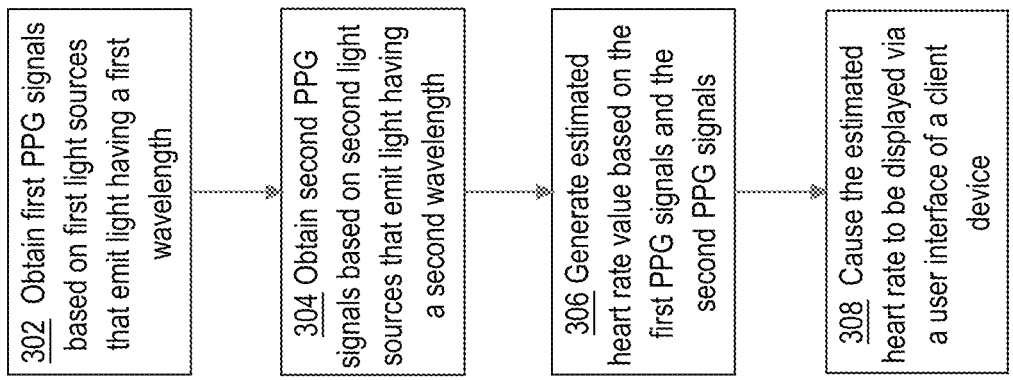
FIG. 3 illustrates an example method of generating an estimated heart rate using a plurality of PPG signals.

FIG. 3 illustrates an example method of generating an estimated heart rate using a plurality of PPG signals. At block 302, the method obtains first PPG signals based on first light sources that emit light having a first wavelength. The first PPG signals may be obtained from the detectors based upon light sources operating at any of the frequencies that have been described above. For example, by executing instructions stored in memory 112 (FIG. 1B) as control program 118, CPU 110 signals driver 122 to activate light sources G1, G2, which produce light directed toward blood vessels which is reflected to detector 106. The detector 106 produces a responsive signal to bus 116 that is gated to CPU 110 via driver 122 and then stored in a register of the CPU or in memory 112. The first PPG signals may be represented in any suitable form capable of being processed by a processor, such as the analog signals or digital data sampled from the analog components and stored in computer memory. In an example, the first PPG signals may correspond to green light previously emitted by a light source (or light sources) after the emitted light has interacted with a user's skin, when the monitoring device is worn, and the first PPG signals may include a motion component.

At block 304, the method obtains second PPG signals based on second light sources that emit length having a second wavelength. For example, in a manner similar to that described above for block 302, the CPU 110 drives light sources R1, R2 and obtains second PPG signals from the detector 106 based upon those light sources. Again, the second set of PPG signals may be represented in any suitable form capable of being processed by a processor, such as the analog signals or digital data sampled from the analog components and stored in computer memory. In an example, the second PPG signals are obtained from different ranges of wavelengths emitted from the light source than the first PPG signals. For example, the second PPG signals may be obtained from red and/or infrared light sources.

Since the methods of FIG. 3, as well as FIG. 4A, FIG. 4B as described below, may be used with any of the embodiments previously described, obtaining signals at block 302, 304 may include obtaining one or more of the first PPG signals using the first light sources, or one or more of the second PPG signals using the second light sources, through a diffusion layer or using any of the arrangements of FIG. 1C, FIG. 1D, and FIG. 1E.

At block 306, the method generates an estimated heart rate value based on the first PPG signals and the second PPG signals. Various techniques for generating the heart rate value may be used, as detailed herein for other embodiments. For example, template matching based on a template previously created and stored from a high-quality PPG signal can be used to provide filter coefficients for a matched filter to maximize signal to noise, or an adaptive filter may be used that tunes a band-pass in real-time based upon heartbeat data derived from the PPG datasets, usually based upon green light sources. Once a heart rate estimate is obtained, signals, data values or data points that are available or apparent in the second PPG signals may be used to modify or improve the first PPG signals so that the resulting modified or improved first PPG signals can be transformed into an estimated heart rate value more accurately.

At block 308, the method causes the estimated heart rate value to be displayed via a user interface of a client device. For example, CPU 110 drives display 114 to display the resulting heart rate value. In other embodiments, the method may be programmed to cause uploading the estimated heart rate value to host computer 500 for further processing, display or reporting.

In various implementations of FIG. 3, multiple detectors or detector regions may be used. For example, the method of FIG. 3 may further comprise obtaining the first PPG signals and the second PPG signals using a plurality of discrete detectors each adapted to detect light from different light sources. For example, the method of FIG. 3 may further comprise obtaining the first PPG signals and the second PPG signals using a plurality of discrete detectors each adapted to detect light from different ones of a first green light source (e.g., G1) of a set of green light sources (e.g., first light sources G1, G2), a second green light source (e.g., G2) of the set of green light sources (e.g., first light sources G1, G2), a first red light source (e.g., R1) of a set of red light sources (e.g., second light sources R1, R2), and a second red light source (e.g., R2) of the set of red light sources (e.g., second light sources R1, R2). In some embodiments, the detectors are all the same, but in other embodiments, different detectors are adapted to detect light of different wavelengths, etc.

In one embodiment, a heart rate estimation process recognizes that green light responds much more to oxy-hemoglobin than red light, and therefore PPG signals from green light have a higher cardiac component relative to the motion signal than PPG signals from red light. FIG. 4A illustrates an example method of generating an estimated heart rate using a multi-wavelength PPG sensor that receives a first signal and a second signal. Block 402 represents a start operation or initialization. At block 404, a set of estimator-detector instructions operate on a second signal and generate an output indicating whether, in the second signal, a motion component is relatively high or a cardiac component is relatively high. In an embodiment, green and red light sources are used wherein the first signal corresponds to a green signal and the second signal corresponds to a red signal, and the method uses metrics derived from the red signal to determine if a majority of the red signal is composed of cardiac signal or motion signal.

If a majority of the second signal is composed of a cardiac signal, then no correction is performed and only the first signal, which could be based upon a green light source, is used for heart rate estimation as seen at block 406.

If, however, a majority of the second signal is a motion signal, then at block 408 a correction is performed using any of several approaches. In one embodiment, the method determines an approximate scaling and translation factor between the red and green signals for given windows of time, and then subtracts the transformed red signal from the green signal. In another embodiment, an optimal linear transform is applied to the red signal before subtracting from the green signal such that it removes all components of motion present in the green signal and leaves only the cardiac components. Other techniques that can be used include, but are not limited to, independent component analysis (ICA) and other forms of blind source separation. The heart rate estimation can then be performed using the modified green signal from which the motion signal has been removed. In some embodiments, a first signal (e.g., green signal) may be modified based on a second signal (e.g., a red signal) as described in connection with operation 408, without first performing operations 404 and 406 (e.g., without determining if the majority of the second signal is composed of a motion signal or a cardiac signal).

In another embodiment, detecting a cardiac component of a PPG signal and detecting a motion component of a PPG signal can be performed based upon signals obtained via different light paths rather than different wavelengths. This embodiment recognizes the discovery that signals obtained via different light paths between light source and detector may have different motion characteristics. For example, signals from a first light path may be known to be more sensitive to cardiac signal or otherwise have a relatively higher cardiac component (in comparison to a motion component), while signals from a second light path may be more sensitive to motion or otherwise have a relatively higher motion component (in comparison to a cardiac component). With such data, the method may use the first light path to sense the cardiac component of a signal and the second, different light path to sense the motion component. Then the techniques otherwise described herein (e.g., see FIG. 4A) may be used to correct or transform the first signal based on the second signal. As a non-limiting example, the second light path may be one where the detector is further away from the emitter in comparison to the first light path. In these embodiments, the light sources that are used to obtain signals via a first light path and a second light path may use the same frequency of light.

In other embodiments, each light source can be individually controlled, or each detector can be individually read out when multiple detectors are used, and such embodiment can collect PPG sensor data along several different light paths. For example, in the arrangement of FIG. 1B, if the control program 118 alternately drives activating on the R1, G1 separately from R2, G2, then the detector 106 can capture two sets of data, namely one for a first light path that is left of the detector and one for a second light path that is right of the detector. The control program 118 can use both sets of data to achieve a more accurate HR estimation. In an embodiment, one such program estimates the signal quality of data obtained on each of the first light path and the second light path and selects to use the higher-quality path for the HR estimation.

Figure 4B:
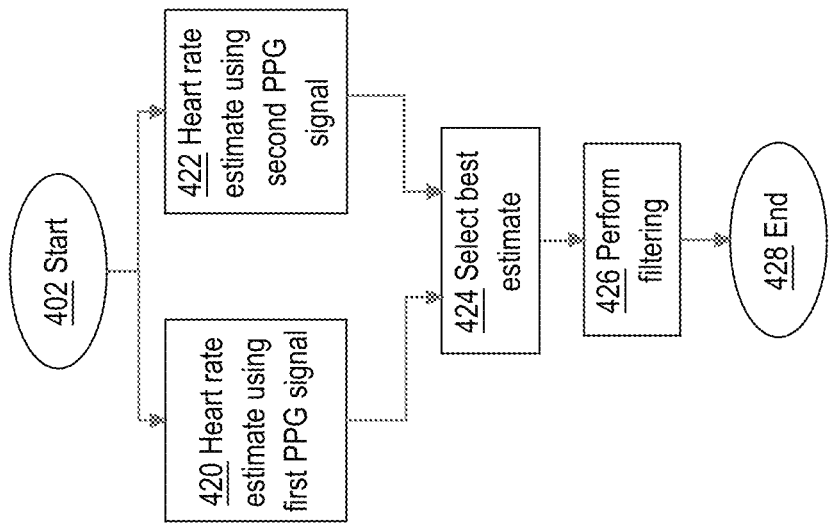
FIG. 4B illustrates an example method of generating an estimated heart rate using a PPG sensor.

FIG. 4B illustrates an example method of generating an estimated heart rate using a multi-position PPG sensor. In other embodiments, more than two channels of PPG sensor data may be used, up to as many light paths as are sensed by the physical hardware.

In the approach of FIG. 4B, an intermediate heart rate estimation is made using signals or data obtained from each the two channels. As seen at block 420 and block 422, after starting at block 402, the method determines a heart rate estimate using the first PPG signal and also determines a separate heart rate estimate using the second PPG signal. In an embodiment, each of blocks 420, 422 produces as output an estimate of the heart rate, for example, in beats-per-minute (BPM) and a confidence value (also referred to herein as a quality metric). In an embodiment, the confidence value is an estimate of the signal quality of the corresponding channel.

At block 424, the method selects between the multiple heart rate estimates. In one embodiment, block 424 comprises selecting one estimate, among those obtained via blocks 420, 422, that has the highest associated confidence value. In an embodiment, the method may use hysteresis logic that prevents jumping between signals of two different channels within a short time window, for example, if the confidence values of both are within a specified tolerance value.

Figure 4A:
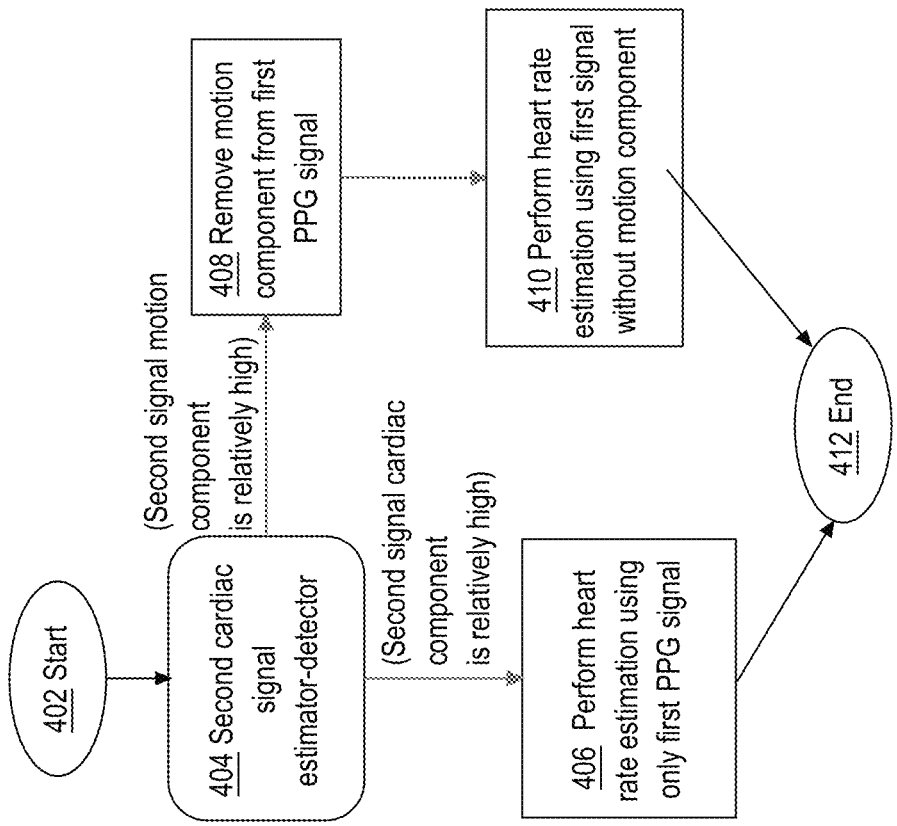
FIG. 4A illustrates an example method of generating an estimated heart rate using a PPG sensor.

In an embodiment, the method may also comprise logic that uses additional context data about the user to bias the selection of heart rate estimate between the two channels, In any of FIG. 3, FIG. 4A, FIG. 4B, the methods may include determining that a user is exercising, and using that determination to influence operation of the methods, such as favoring a signal from either block 420 or block 422 that has a higher heart rate estimate in BPM when the user is known to be exercising. Determining that the user is exercising may occur, for example, using input from an accelerometer that forms part of the apparatus of FIG. 1A, FIG. 1B, FIG. 2, and/or using explicit input indicating that the user is currently exercising (or has just completed exercising, or is about to commence exercising, etc.), that the user has specified using an input device. Or, the system may infer that the user is sleeping, for example based upon accelerometer data, and may select the lower heart rate value in that situation. In one embodiment, the methods may further comprise obtaining motion data from a motion sensor that is proximate to the first light sources and the second light sources; determining that the motion data indicates that a user is performing exercise; in response to determining that the motion data indicates that a user is performing exercise, selecting a higher heart rate value from among the first preliminary estimated heart rate value and the second preliminary estimated heart rate value for use in generating the heart rate value.

Further, in some embodiments, the method may process both the confidence metric and data indicating an exercise state together. For example, in one embodiment, if it is determined that the user is exercising (e.g., if motion sensor data indicates that the user is exercising), then the method may select the highest heart rate estimate if the confidence values of the two estimates are comparable (e.g., if the difference between the two confidence values is less than a predetermined threshold), but the method may also select the lower heart rate estimate if it has a much higher confidence value than the confidence value of the higher HR estimate (e.g., if the difference between the two confidence values is greater than a predetermined threshold).

Thus, in some embodiments, the confidence value may itself be adjusted based on whether the user is exercising. For example, if it is determined the user is exercising, then the confidence value of the higher heart rate estimate may be boosted by a predetermined amount, multiplier, weighting factor, etc. Or, the confidence value of the lower heart rate estimate is decreased in a similar way. Then the method may proceed to select the heart rate estimate with the highest ultimate confidence metric.

At block 426, in one embodiment, a filtering step is used to smooth the selected estimated heart rate value. Filtering can be performed to improve accuracy, or to present a better user experience, or for both.

The approach of FIG. 4B effectively permits the quality of signals to affect selection and use of the signals. More generally, FIG. 4B comprises a method of determining a first quality metric based on the first PPG signals, and a second quality metric based on the second PPG signals; comparing the first quality metric to the second quality metric and selecting either the first quality metric or the second quality metric as a greater quality metric; and generating the estimated heart rate value based on one of the first PPG signals or the second PPG signals that corresponds to the greater quality metric. In one implementation, the quality metric may be a confidence value associated with the signal. Thus, in the method, determining the first quality metric may comprise determining a first confidence value associated with the first PPG signals, the first confidence value indicating a quality of a first preliminary estimated heart rate value generated based on the first PPG signals, and determining the second quality metric comprises determining a second confidence value associated with the second PPG signals, the second confidence value indicating a quality of a second preliminary estimated heart rate value generated based on the second PPG signals. In some alternative embodiments, the quality metric described herein can be determined based on the ratio of cardiac signal magnitude to non-cardiac (e.g., noise) signal magnitude.

In some embodiments, a magnitude of a heart rate or other quality metrics can be used. For example, the method can comprise obtaining motion data from a motion sensor that is proximate to the first light sources and the second light sources, and determining that the motion data indicates that a user is performing exercise. Then, in response to determining that the motion data indicates that a user is performing exercise, the method can select a higher heart rate value from among the first preliminary estimated heart rate value and the second preliminary estimated heart rate value for use in generating the heart rate value.

In one feature of this approach, a method (e.g., the method of FIG. 4B) can include selectively activating one or more of the first light sources and one or more of the second light sources at different times.

Using these approaches, extra information gathered from one PPG signal may be used to improve the accuracy of estimating a heart rate value from another PPG signal, especially when the user is exercising or performing high-motion activities. Further, the PPG signals may be processed with more robustness to motion, and therefore the monitoring device 100 may be designed or engineered to accommodate less strict inactivity requirements as a basis for obtaining a useful heart rate value. For example, the monitoring device may be, in some cases, capable of accommodating a less snug attachment to the body, and/or the monitoring device may, in some cases, be capable of accommodating greater levels of exercise or other activity that otherwise would interfere with obtaining accurate heart rate values using the monitoring device when mounted on the body.

In various embodiments, the methods of FIG. 3, FIG. 4A, FIG. 4B may be performed by one or more of: firmware operating on the monitoring device or a secondary device, such as a mobile device paired to the monitoring device, a server, host computer 500, and the like. For example, the monitoring device may execute operations relating to generating the PPG signals which are uploaded or otherwise communicated to a server that performs operations for removing the motion components and creating a final heart rate estimate value. Alternatively, the monitoring device may execute operations relating to generating the PPG signals and removing the motion components to produce a final heart rate estimate value local to the monitoring device 100. In this case, the final heart rate estimate may be uploaded or otherwise communicated to a server such as host computer 500 that performs other operations using the value.

While various examples herein describe obtaining first PPG signals based on first light sources (e.g., green light sources) and obtaining second PPG signals based on second light sources (e.g., red or IR light sources), a monitoring device may apply the techniques described herein to obtain PPG signals from more than two types of light sources for the purposes of generating an estimated heart rate value. For example, in some embodiments, a monitoring device may obtain first PPG signals based on first light sources (e.g., green light sources), obtain second PPG signals based on second light sources (e.g., red light sources), and also obtain third PPG signals based on third light sources (e.g., IR light sources) that are configured to emit light having a third light wavelength, and generate an estimated heart rate value based on data obtained from any one or more of the first, second, and third PPG signals.

In some embodiments, the monitoring device described herein may switch between obtaining PPG signals from different wavelengths based on the user's skin pigmentation in order to generate a more accurate heart rate estimate. For example, since red wavelengths are less attenuated by melanin, it is possible that a better qualify heart rate signal can be obtained via the red channel from users with high melanin content in their skin. In some embodiments, a monitoring device may determine the skin pigmentation of the user based on an imaging sensor or ambient light detector included in the monitoring device, or based on explicit user input (e.g., indicating skin tone) received via the monitoring device or an input device connected to the monitoring device. Accordingly, if the CPU 110 or control program 118 described herein determines that the skin pigmentation of the user satisfies one or more rules or conditions (e.g., if the user's skin pigmentation can be classified as a specific skin pigmentation having a high melanin content), then the CPU 110 or control program 118 may selectively obtain PPG signals based on red light sources for the purposes of determining heart rate, consistent with the techniques described herein.

In an embodiment, the use of multiple light sources or other emitters in configurations that are spaced differently with respect to the detector permits the monitoring device 100 to control the effective detector-light source spacing to optimize for signal strength under various user skin conditions, by activating different pairs of light sources. As the detector-light source spacing increases, for example, a light path between the light source and detector samples tissue content over a longer and deeper path, thereby improving signal strength. For example, users who exhibit periods of time of low perfusion, due to conditions such as cooling of the skin, may benefit from increasing the light source-detector spacing automatically under program control, by activating the red light sources that are farther away from the detector. The same effect can be obtained using a single emitter and a plurality of detectors.

Additionally or alternatively, the process of FIG. 3, FIG. 4A, FIG. 4B may receive input from biometric sensors or environmental sensors indicating an ambient temperature or a skin temperature of the wearer of the activity monitoring apparatus. Based on changes in temperature values received from these sensors, the process may energize or de-energize different pairs of light sources. In this embodiment, the process of FIG. 3, FIG. 4A, FIG. 4B may include: activating only a first pair of two or more pairs of red light sources and green light sources, and deactivating all other pairs; receiving, from the one or more detectors, a first red PPG signal and a first green PPG signal from only the first pair of the two or more pairs of red light sources and green light sources; receiving an ambient temperature signal from an ambient temperature sensor that is located proximate to the two or more first pairs; determining that the ambient temperature signal is less than a stored minimum temperature signal; based on the determining, activating a second pair of the two or more pairs of red light sources and green light sources, receiving from the one or more detectors a second red PPG signal and a second green PPG signal associated with the second pair, forming a combined red PPG signal using the first red PPG signal and the second red PPG signal, and forming a combined green PPG signal using the first green PPG signal and the second green PPG signal.

The processes of FIG. 3, FIG. 4A, FIG. 4B also may include a feedback loop and other test operations that result in selectively energizing or de-energizing different pairs of red and green light sources of the monitoring device 100 as ambient conditions change. For example, the processes of FIG. 3, FIG. 4A, FIG. 4B may be implemented as part of a continuous loop that is active whenever the monitoring device 100 is powered on, and may include operations to de-energize the second pair of light sources when signals received from the first pair of light sources are determined to be greater than the stored minimum signal value. Further, the process as a whole may be repeated for any one or more pairs of the light sources, so that the process results in energizing three or more pairs of light sources at any one time. In this manner, over time, different combinations of pairs may be energized or de-energized dynamically in response to changing ambient conditions, changing skin temperature, movement of the monitoring device 100 on the body of the user, or other conditions that result in changes in the strength of signals from the light sources.

4. Implementation Example—Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 5:
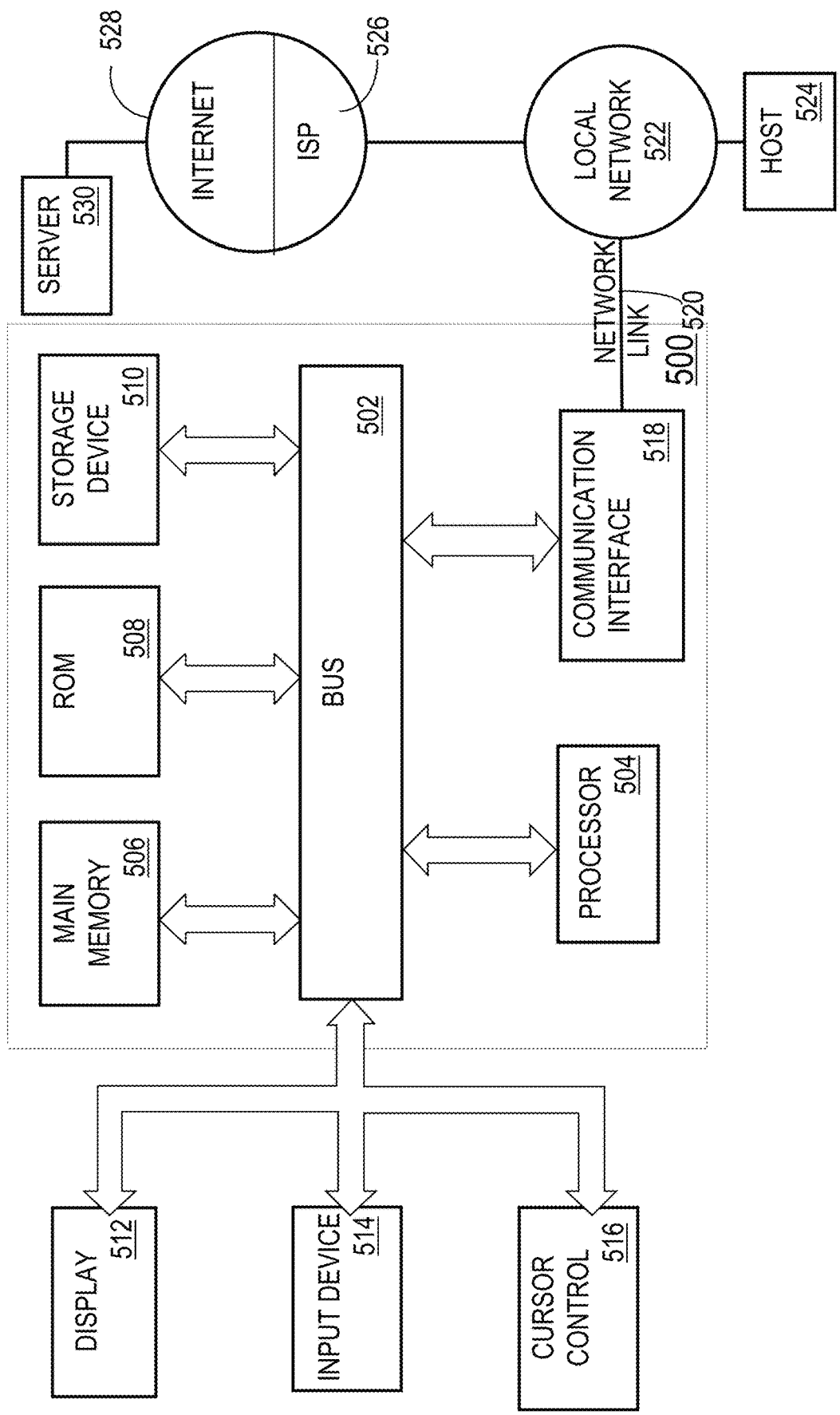
FIG. 5 illustrates an example computer system that may be specially configured to perform various techniques described herein.

For example, FIG. 5 is a block diagram that illustrates a computer system 500 upon which an embodiment may be implemented. Computer system 500 includes a bus 502 or other communication mechanism for communicating information, and a hardware processor 504 coupled with bus 502 for processing information. Hardware processor 504 may be, for example, a general purpose microprocessor.

Computer system 500 also includes a main memory 506, such as a random access memory (RAM) or other dynamic storage device, coupled to bus 502 for storing information and instructions to be executed by processor 504. Main memory 506 also may be used for storing temporary variables or other intermediate information during execution of instructions to be executed by processor 504. Such instructions, when stored in non-transitory storage media accessible to processor 504, render computer system 500 into a special-purpose machine that is customized to perform the operations specified in the instructions.

Computer system 500 further includes a read only memory (ROM) 508 or other static storage device coupled to bus 502 for storing static information and instructions for processor 504. A storage device 510, such as a magnetic disk, optical disk, or solid-state drive is provided and coupled to bus 502 for storing information and instructions.

Computer system 500 may be coupled via bus 502 to a display 512, such as a cathode ray tube (CRT), for displaying information to a computer user. An input device 514, including alphanumeric and other keys, is coupled to bus 502 for communicating information and command selections to processor 504. Another type of user input device is cursor control 516, such as a mouse, a trackball, or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane.

Computer system 500 may implement the techniques described herein using customized hard-wired logic, one or more ASICs or FPGAs, firmware and/or program logic which in combination with the computer system causes or programs computer system 500 to be a special-purpose machine. According to one embodiment, the techniques herein are performed by computer system 500 in response to processor 504 executing one or more sequences of one or more instructions contained in main memory 506. Such instructions may be read into main memory 506 from another storage medium, such as storage device 510. Execution of the sequences of instructions contained in main memory 506 causes processor 504 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 510. Volatile media includes dynamic memory, such as main memory 506. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 502. Transmission media can also take the form of acoustic or light waves, such as those generated during radio-wave and infra-red data communications.

Various forms of media may be involved in carrying one or more sequences of one or more instructions to processor 504 for execution. For example, the instructions may initially be carried on a magnetic disk or solid-state drive of a remote computer. The remote computer can load the instructions into its dynamic memory and send the instructions over a telephone line using a modem. A modem local to computer system 500 can receive the data on the telephone line and use an infra-red transmitter to convert the data to an infra-red signal. An infra-red detector can receive the data carried in the infra-red signal and appropriate circuitry can place the data on bus 502. Bus 502 carries the data to main memory 506, from which processor 504 retrieves and executes the instructions. The instructions received by main memory 506 may optionally be stored on storage device 510 either before or after execution by processor 504.

Computer system 500 also includes a communication interface 518 coupled to bus 502. Communication interface 518 provides a two-way data communication coupling to a network link 520 that is connected to a local network 522. For example, communication interface 518 may be an integrated services digital network (ISDN) card, cable modem, satellite modem, or a modem to provide a data communication connection to a corresponding type of telephone line. As another example, communication interface 518 may be a local area network (LAN) card to provide a data communication connection to a compatible LAN. Wireless links may also be implemented. In any such implementation, communication interface 518 sends and receives electrical, electromagnetic or optical signals that carry digital data streams representing various types of information.

Network link 520 typically provides data communication through one or more networks to other data devices. For example, network link 520 may provide a connection through local network 522 to another host computer 524 or to data equipment operated by an Internet Service Provider (ISP) 526. ISP 526 in turn provides data communication services through the world wide packet data communication network now commonly referred to as the "Internet" 528. Local network 522 and Internet 528 both use electrical, electromagnetic or optical signals that carry digital data streams. The signals through the various networks and the signals on network link 520 and through communication interface 518, which carry the digital data to and from computer system 500, are example forms of transmission media.

Computer system 500 can send messages and receive data, including program code, through the network(s), network link 520 and communication interface 518. In the Internet example, a server 530 might transmit a requested code for an application program through Internet 528, ISP 526, local network 522 and communication interface 518.

The received code may be executed by processor 504 as it is received, and/or stored in storage device 510, or other non-volatile storage for later execution.

In the foregoing specification, embodiments have been described with reference to numerous specific details that may vary from implementation to implementation. The specification and drawings are, accordingly, to be regarded in an illustrative rather than a restrictive sense. The sole and exclusive indicator of the scope of the disclosure, and what is intended by the applicants to be the scope of the disclosure, is the literal and equivalent scope of the set of claims that issue from this application, in the specific form in which such claims issue, including any subsequent correction.

What is claimed is:

1. An activity monitoring apparatus comprising:
   one or more first light sources that are configured to emit light having a first light wavelength corresponding to a green light wavelength;
   one or more second light sources that are configured to emit light having a second light wavelength corresponding to a red light wavelength, wherein one or more of the one or more first light sources and one or more of the one or more second light sources are co-located;
   one or more processors;
   a non-transitory computer-readable storage medium coupled to the one or more processors and storing instructions which, when executed using the one or more processors, cause the one or more processors to:
      obtain one or more first photoplethysmography (PPG) signals based on light emitted from the one or more first light sources;
      obtain one or more second PPG signals based on light emitted from the one or more second light sources;
      determine that a majority of the one or more second PPG signals are comprised of motion signals;
      responsive to determining that the majority of the one or more second PPG signals are comprised of motion signals, remove corresponding motion signals from the one or more first PPG signals;
      generate an estimated heart rate value based on only the one or more first PPG signals after the corresponding motion signals have been removed from the one or more first PPG signals; and
      cause the estimated heart rate value to be displayed via a user interface.

2. The activity monitoring apparatus of claim 1, wherein the non-transitory computer-readable storage medium further stores one or more additional instructions which, when executed using the one or more processors, further cause the one or more processors to remove the corresponding motion signals from the one or more first PPG signals using an independent component analysis of the one or more first PPG signals and the one or more second PPG signals.

3. The activity monitoring apparatus of claim 1, wherein the non-transitory computer-readable storage medium further stores one or more additional instructions which, when executed using the one or more processors, further cause the one or more processors to remove the corresponding motion signals from the one or more first PPG signals by:
   transforming the one or more second PPG signals by at least one of a scaling and translation factor, and
   subtracting the transformed one or more second PPG signals from the first PPG signals.

4. The activity monitoring apparatus of claim 1, further comprising:
   a first detector; and
   a second detector, wherein:
      the first detector and the second detector are located at different locations having different light paths with respect to at least one of the one or more first light sources and with respect to at least one of the one or more second light sources, and
      the non-transitory computer-readable storage medium further stores one or more instructions which, when executed using the one or more processors, further cause the one or more processors to:
         obtain at least one PPG signal selected from the group consisting of: the one or more first PPG signals and the one or more second PPG signals using the first detector; and obtain at least one PPG signal selected from the group consisting of: the one or more first PPG signals and the one or more second PPG signals using the second detector.

5. The activity monitoring apparatus of claim 1, wherein at least one of the one or more first light sources and at least one of the one or more second light sources comprise discrete light-emitting diode (LED) emitters.

6. The activity monitoring apparatus of claim 1, wherein one or more of the one or more first light sources and one or more of the one or more second light sources collectively comprise a single multi-color light-emitting diode (LED).

7. The activity monitoring apparatus of claim 6, wherein the single multi-color LED is a red-green-infrared LED.

8. The activity monitoring apparatus of claim 1, wherein:
the activity monitoring apparatus is configured to align the one or more first light sources adjacent to blood vessels of a human when worn on a body location of the human selected from the group consisting of: a wrist, an ear, and a head, and the non-transitory computer-readable storage medium further stores one or more additional instructions which, when executed using the one or more processors, further cause the one or more processors to obtain the one or more first PPG signals based on light from the one or more first light sources when the activity monitoring apparatus is worn on the body location.

9. The activity monitoring apparatus of claim 1, further comprising a first detector having a first side and a second side opposite the first side, wherein:
the one or more first light sources include a first green light source and a second green light source,
the one or more second light sources include a first red light source and a second red light source,
the first green light source and the first red light source are at the first side of the first detector,
the second green light source and the second red light source are at the second side of the first detector, and
the non-transitory computer-readable storage medium further stores one or more additional instructions which, when executed using the one or more processors, further cause the one or more processors to:
obtain the one or more first PPG signals based on emission of green light from the first green light source and the second green light source; and
obtain the one or more second PPG signals based on emission of red light from the first red light source and the second red light source.

10. The activity monitoring apparatus of claim 9, wherein at least the first green light source and the first red light source are co-located so as to emit light on a common light path toward the first detector.

11. The activity monitoring apparatus of claim 9, wherein both the first green light source and the first red light source are in a common light source package.

12. The activity monitoring apparatus of claim 9, wherein a diffusion layer is positioned over at least the first green light source and the first red light source.

13. The activity monitoring apparatus of claim 9, wherein the first detector is one of a plurality of discrete detectors that are configured to detect light emitted from the first green light source, the second green light source, the first red light source, and the second red light source.

14. The activity monitoring apparatus of claim 9, wherein:
the first detector is further away from the second green light source and the second red light source than the first green light source and the first red light source.

15. The activity monitoring apparatus of claim 1, wherein the non-transitory computer-readable storage medium further stores one or more additional instructions which, when executed using the one or more processors, further cause the one or more processors to:
selectively activate at least one of the one or more first light sources and at least one of the one or more second light sources at different times.

16. The activity monitoring apparatus of claim 1, wherein the non-transitory computer-readable storage medium further stores one or more additional instructions which, when executed using the one or more processors, further cause the one or more processors to:
obtain one or more third PPG signals based on light emitted from one or more third light sources that are configured to emit light having a third light wavelength, wherein the third light wavelength is an infrared wavelength; and
modify the estimated heart rate value based on data obtained from the one or more third PPG signals.

17. The activity monitoring apparatus of claim 1, wherein:
the one or more first light sources include a first green light source and a second green light source; and
the non-transitory computer-readable storage medium further stores one or more additional instructions which, when executed using the one or more processors, cause the one or more processors to obtain the one or more first PPG signals based on emission of green light from the first green light source and, at a different time, emission of green light from the second green light source.

18. The activity monitoring apparatus of claim 1, wherein the one or more second light sources include a first red light source and a second red light source; and
the non-transitory computer-readable storage medium further stores one or more additional instructions which, when executed using the one or more processors, cause the one or more processors to obtain the one or more first PPG signals based on emission of red light from the first red light source and, at a different time, emission of red light from the second red light source.

19. The activity monitoring apparatus of claim 1, wherein the non-transitory computer-readable storage medium further stores one or more additional instructions which, when executed using the one or more processors, further cause the one or more processors to cause the estimated heart rate value to be displayed via a user interface on a client device.

20. A method of estimating a heart rate for a user, the method comprising:
obtaining, by one or more processors, one or more first photoplethysmography (PPG) signals based on light emitted from one or more first light sources of an activity monitoring apparatus worn by the user, the one or more first light sources configured to emit light having a first light wavelength corresponding to a green light wavelength;
obtaining, by the one or more processors, one or more second PPG signals from one or more second light sources of the activity monitoring apparatus, the one or more second light sources configured to emit light having a second wavelength corresponding to a red light wavelength;

determining, by the one or more processors, that a majority of the one or more second signals are comprised of motion signals;

responsive to determining that the majority of the one or more second PPG signals are comprised of motion signals, removing, by the one or more processors, corresponding motion signal from the one or more first PPG signals; and generating, by the one or more processors, an estimated heart rate value for the user based on the one or more first PPG signals after the corresponding motion signals have been removed therefrom; and causing, by the one or more processors, the estimated heart rate value to be displayed on a user interface.

* * * * *